United States Patent
Biswas et al.

(10) Patent No.: US 12,221,403 B2
(45) Date of Patent: Feb. 11, 2025

(54) $N^\varepsilon$-LONG CHAIN ACYL LYSINE CRYSTAL PRODUCTION METHOD AND COMPOSITION CONTAINING SAID CRYSTALS

(71) Applicant: AJINOMOTO CO., INC., Tokyo (JP)

(72) Inventors: Shuvendu Biswas, Kawasaki (JP); Naoya Yamato, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 627 days.

(21) Appl. No.: 17/646,027

(22) Filed: Dec. 27, 2021

(65) Prior Publication Data
US 2022/0119343 A1    Apr. 21, 2022

Related U.S. Application Data

(63) Continuation of application No. PCT/JP2020/024572, filed on Jun. 23, 2020.

(30) Foreign Application Priority Data

Jun. 27, 2019    (JP) ............................. 2019-119387

(51) Int. Cl.
  *C07C 233/47*    (2006.01)
  *A61K 8/02*    (2006.01)
  *A61K 8/42*    (2006.01)

(52) U.S. Cl.
  CPC ............ *C07C 233/47* (2013.01); *A61K 8/022* (2013.01); *A61K 8/42* (2013.01); *A61K 2800/622* (2013.01); *C07B 2200/13* (2013.01)

(58) Field of Classification Search
  CPC .. C07C 233/47; C07C 231/24; C07B 2200/13
  See application file for complete search history.

(56) References Cited

U.S. PATENT DOCUMENTS

| 4,640,943 | A | 2/1987 | Meguro et al. |
| 6,555,708 | B1 * | 4/2003 | Yamato .................... A61K 8/02 |
| | | | 401/126 |
| 10,266,857 | B2 * | 4/2019 | Takakura ................. C12N 9/80 |
| 2011/0048284 | A1 | 3/2011 | Choi et al. |

FOREIGN PATENT DOCUMENTS

| JP | 61-010503 A | 1/1986 |
| JP | 63-017972 A | 1/1988 |
| JP | 01/242563 A | 9/1989 |

(Continued)

OTHER PUBLICATIONS

International Search Report in PCT/JP2020/024572 dated Sep. 8, 2020.

*Primary Examiner* — Yate' K Cutliff
(74) *Attorney, Agent, or Firm* — Oblon, McClelland, Maier & Neustadt, L.L.P.

(57) ABSTRACT

An unground $N^\varepsilon$-long chain acyl lysine crystal production method that includes: preparing a solution having at least one type of $N^\varepsilon$-long chain acyl lysine dissolved in an acidic or basic solvent including water and/or one type selected from water-soluble organic solvents; dipping the solution into an acidic solution having a pH of at least 0.2 and less than 2.0, at a temperature of no more than 20° C.; and crystallizing $N^\varepsilon$-long chain acyl lysine crystals.

21 Claims, 13 Drawing Sheets

(56) References Cited

FOREIGN PATENT DOCUMENTS

| | | | |
|---|---|---|---|
| JP | 04-63844 B2 | 10/1992 | |
| JP | 08-337519 A | 12/1996 | |
| JP | H08337519 A * | 12/1996 | ............... A61K 8/00 |
| JP | 09-323914 A | 12/1997 | |
| JP | 2008-214341 A | 9/2008 | |
| JP | 2010-242026 A | 10/2010 | |
| JP | 4826049 B2 | 9/2011 | |
| WO | 2001/14317 A1 | 3/2001 | |
| WO | 2011/025252 A2 | 3/2011 | |

* cited by examiner

EXAMPLE 3-2 | COMPARATIVE EXAMPLE 3-10 | COMPARATIVE EXAMPLE 3-17 | COMPARATIVE EXAMPLE 3-2

COMPARATIVE EXAMPLE 3-24 | EXAMPLE 3-3 | COMPARATIVE EXAMPLE 3-3

EXAMPLE 3-4 | EXAMPLE 3-5

EXAMPLE 3-6    EXAMPLE 3-7    EXAMPLE 3-8

COMPARATIVE EXAMPLE 3-25    EXAMPLE 3-9

COMPARATIVE EXAMPLE 3-26    EXAMPLE 3-10

COMPARATIVE EXAMPLE 3-32    EXAMPLE 3-17

COMPARATIVE EXAMPLE 3-33    EXAMPLE 3-18

COMPARATIVE EXAMPLE 3-34    EXAMPLE 3-19    EXAMPLE 3-20

| COMPARATIVE EXAMPLE 3-35 | EXAMPLE 3-21 | COMPARATIVE EXAMPLE 3-8 |

COMPARATIVE EXAMPLE 3-37

| COMPARATIVE EXAMPLE 5-1 | COMPARATIVE EXAMPLE 5-2 | EXAMPLE 5 |

10 MINUTES LATER

COMPARATIVE EXAMPLE 3-24 | EXAMPLE 3-3 | COMPARATIVE EXAMPLE 3-39 | COMPARATIVE EXAMPLE 3-22

20 MINUTES LATER

COMPARATIVE EXAMPLE 3-35 | EXAMPLE 3-21 | COMPARATIVE EXAMPLE 3-8

7 MINUTES LATER

COMPARATIVE EXAMPLE 3-29 | EXAMPLE 3-15 | COMPARATIVE EXAMPLE 3-14

5 MINUTES LATER

5 MINUTES LATER

FIG.26
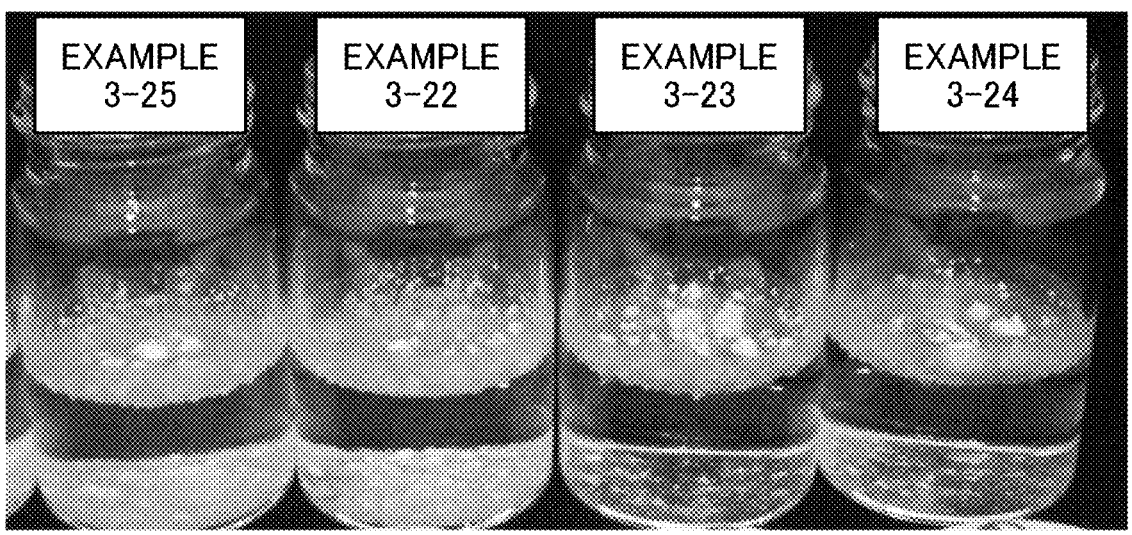
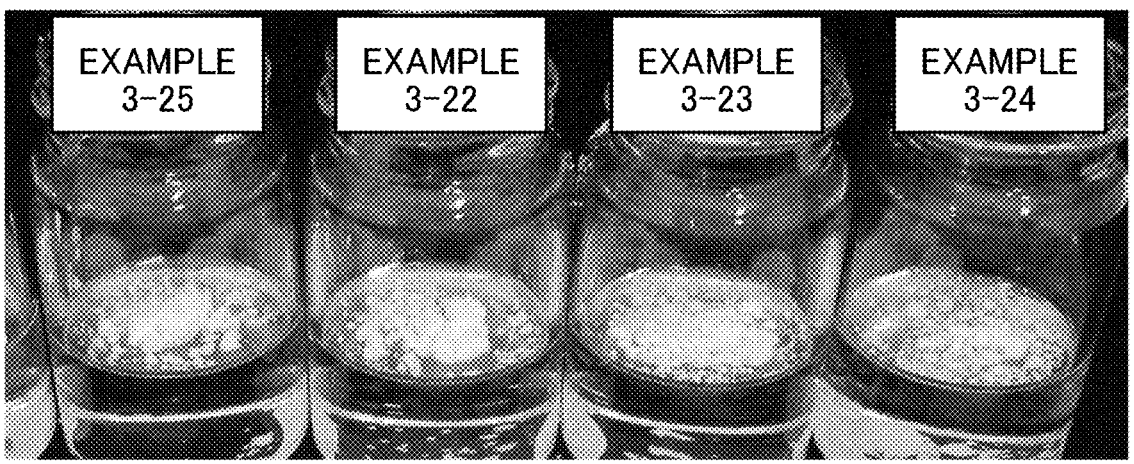

$N^\varepsilon$-LONG CHAIN ACYL LYSINE CRYSTAL PRODUCTION METHOD AND COMPOSITION CONTAINING SAID CRYSTALS

CROSS REFERENCES TO RELATED APPLICATIONS

This application is a continuation of International Patent Application No. PCT/JP2020/024572, filed on Jun. 23, 2020, and claims priority to Japanese Patent Application No. 2019-119387, filed on Jun. 27, 2019, both of which are incorporated herein by reference in their entireties.

BACKGROUND OF THE INVENTION

Field of the Invention

The present invention relates to $N^\varepsilon$-long chain acyl lysine crystal production methods and compositions containing said crystals.

Discussion of the Background

Powder raw materials that can simultaneously exhibit the performances, water repellency and oil repellency, are important for cosmetic products and various industrial applications. However, it has been difficult to obtain inexpensive and environmentally friendly powder raw materials that can simultaneously exhibit these functions.

For example, inorganic powders such as talc, mica, sericite, titanium oxide, zinc oxide, iron oxide, aluminum oxide, barium sulfate, boron nitride, silica, and synthetic gold mica (synthetic mica), and organic powders such as starch, cellulose, fatty acid salts, and bamboo and wood powders are used to impart lubricity, improve hiding power, color, and absorb or scatter light. In general, because of the presence of highly polar functional groups on the surface of powders, powders are easily wetted by highly polar solvents such as water. However, when used in cosmetic products, such powders get wet with sweat, causing dullness and discoloration of the makeup. They also run off with sweat, causing the makeup to smudge. In industrial applications as well, there are problems that paints and inks containing these powders get wet in water or rain and run off, and when used as lubricants for machinery and the like, they do not exhibit sufficient lubricity.

Also, ordinary powders do not have excellent oil repellency either, so that when they are used in cosmetic products and the like, the surface of the powders gets wet with sebum and the like, causing discoloration and dullness of cosmetic products such as foundations (see Japanese Patent Application Publication No. 2010-242026, which is incorporated herein by reference in its entirety). In addition, when absorbing oil, they cause the makeup to smudge. In industrial applications as well, there are problems that when used as lubricants, they also cause problems such as absorbing oil from machinery and creating a high viscosity mud-like stain.

In order to solve these problems, a technique has been developed to treat the surface of powders with fluorine-containing molecules that do not dissolve in either water or oil. Although powders treated with fluorine-containing molecules exhibit excellent properties in water repellency and oil repellency, the presence of per-fluorine compounds and low molecular weight fluorine compounds as impurities raises the issue of accumulation and toxicity in the environment and human body. In addition, there is a problem that powders surface-treated with fluorine-containing molecules do not blend well with the skin, and do not provide excellent makeup lasting or use feel. Furthermore, there is a problem that since the oil repellency of powders treated with fluorine-containing molecules is extremely reduced in the presence of water, the powders get wet with sweat and sebum when used in cosmetic products.

Studies have been conducted in which $N^\varepsilon$-lauroyl lysine crystals, a raw material derived from amino acids that does not disperse in water, does not dissolve in oil, and moreover does not accumulate in the environment, have been attached to the surface of powders to add the functions of $N^\varepsilon$-lauroyl lysine crystals to the powders. It is important that the surface of the powder be completely covered with $N^\varepsilon$-lauroyl lysine crystals. However, while the 90% particle diameter D90 (number-based distribution) of common powders is often less than 20 µm, the commercially available $N^\varepsilon$-lauroyl lysine crystals ("Amihope LL" manufactured by Ajinomoto Co., Inc.) have a 90% particle diameter D90 (number-based distribution) of 15.7 µm, and the median diameter and average particle diameter of the volume-based distribution are 14.3 µm and 15.3 µm, respectively. In addition, the median diameter of the volume-based distribution of $N^\varepsilon$-octanoyl lysine crystals ("Amihope" OL manufactured by Ajinomoto Co., Inc.) is 20 µm. Since these crystals contain few crystals with small particle diameter, it is difficult that common powders are stably coated by $N^\varepsilon$-lauroyl lysine crystals or $N^\varepsilon$-octanoyl lysine crystals by simple mixing from the DLVO theory. For example, a simple dry treatment method is known in which the powder is simply mixed with $N^\varepsilon$-lauroyl lysine crystals and the surface of the powder is treated with $N^\varepsilon$-lauroyl lysine crystals (see International Publication No. 2011/025252, which is incorporated herein y reference in its entirety). However, in this method, the coverage rate of $N^\varepsilon$-lauroyl lysine crystals is poor, and as a result, sufficiently excellent water repellency and oil repellency cannot be achieved.

Also, in order to improve the coverage rate of $N^\varepsilon$-lauroyl lysine crystals, a method has been studied that creates a fine powder of $N^\varepsilon$-lauroyl lysine crystals, simply mixes this fine powder with powder, and treats the surface of the powder with $N^\varepsilon$-lauroyl lysine crystals. For example, it is known that $N^\varepsilon$-lauroyl lysine crystals are finely ground by the wet grinding method (see Japanese Patent Application Publication No. Hei 09-323914 and Japanese Patent No. 4826049, which are incorporated herein by reference in their entireties) and mixed with inorganic powder. However, to obtain a fine powder of $N^\varepsilon$-lauroyl lysine crystals by this method, it is necessary to grind the crystals more than 20 times, making it difficult to produce a fine powder of $N^\varepsilon$-lauroyl lysine crystals on a large industrial scale. Also, even after grinding more than 20 times, the average particle diameter of the obtained $N^\varepsilon$-lauroyl lysine crystals (volume-based distribution) is 3.4 µm, and even when these crystals are mixed with inorganic powder and the inorganic powder is treated with $N^\varepsilon$-lauroyl lysine crystals, it is impossible to achieve sufficiently excellent water repellency and oil repellency. Furthermore, this method requires the use of a large amount of organic solvent, which makes it difficult to produce at low cost and has a high environmental impact.

It has been reported that in order to obtain fine crystals of $N^\varepsilon$-lauroyl lysine by a simpler method, a basic solution of $N^\varepsilon$-lauroyl lysine is added dropwise to a solution such as hydrochloric acid having a pH maintained at 2 to 5 followed by crystallization, crystals of $N^\varepsilon$-lauroyl lysine with an average projected diameter of 0.5 µm were obtained (see Japanese Patent Application Publication No. Hei 08-337519, which is incorporated herein by reference in its entirety). By mixing these crystals with powder, the adhesion of the mixed powder to the skin and the use feel of the mixed powder can be improved. However, it has been found that the water repellency and oil repellency of the mixed powder obtained by this method is not improved, and on the contrary, the dispersibility of the powder in water or oil is increased. Furthermore, it is reported that when the crystals of $N^\varepsilon$-lauroyl lysine obtained using this method are measured by a laser diffraction/scattering particle diameter distribution measurement device, the average particle diameter (volume-based distribution) is 18 μm (see Production Comparison Example 2 in Japanese Patent No. 4826049, which is incorporated herein by reference in its entirety). Specifically, the reason why the water repellency and oil repellency of the powder cannot be improved by using the $N^\varepsilon$-lauroyl lysine crystals obtained by this method is that the particle diameter of the mixed $N^\varepsilon$-lauroyl lysine crystals is large. In the case of plate-shaped particles, there may be a difference between the projected diameter measured with a microscope and the average particle diameter measured by the light scattering method or the like due to the principles of measurement.

In addition, $N^\varepsilon$-lauroyl lysine crystals with an average particle diameter (volume-based distribution) of 3 to 15 μm are obtained by crystallization at pH 7.0 (see Japanese Patent No. 4826049, which is incorporated herein by reference in its entirety). However, treatment of powders with the $N^\varepsilon$-lauroyl lysine crystals obtained by this method does not achieve sufficiently excellent water repellency and oil repellency.

It is also known that $N^\varepsilon$-lauroyl lysine can be attached to the surface of powder by wet treatment (see Japanese Examined Patent Application Publication No. Hei 4-63844 and Japanese Patent Application Publication No. Sho 61-10503, which are incorporated herein by reference in their entireties). Since $N^\varepsilon$-lauroyl lysine itself is sparingly soluble, it can once be dissolved in a strong alkali, strong acid, or solvent, and the solution can be gradually added to an acid or alkaline powder dispersion to neutralize and crystallize $N^\varepsilon$-lauroyl lysine on the surface of the powder in the powder dispersion. By filtering and drying the dispersion after crystallization, it is possible to obtain a powder with $N^\varepsilon$-lauroyl lysine attached to the surface thereof. However, even when an inorganic powder is treated with $N^\varepsilon$-lauroyl lysine by this method, a certain degree of water repellent and oil repellent functions can be obtained, but it cannot be said that the degree is sufficient. In addition, this method requires the use of a large number of organic solvent and repeated dissolution and drying treatments, leading to a problem that it is difficult to produce at low cost. Furthermore, in the case of silica, starch, and other powders that dissolve in solvents, acids, or alkalis, there is also a problem that the surface of the powder cannot be treated with $N^\varepsilon$-lauroyl lysine crystals or $N^\varepsilon$-octanoyl lysine crystals.

Also, another possibility is to use a special composite treatment machine to strongly collide the powder with $N^\varepsilon$-lauroyl lysine crystals, thereby using the shearing force of the machine to treat the surface of the powder with $N^\varepsilon$-lauroyl lysine crystals. However, this method has the problem that the amount of powder that can be treated at one time is small and cannot be produced inexpensively. In addition, there is also a problem that brittle powders such as silica are ground, which reduces the unique functions of the powder. Furthermore, there is a problem that it is impossible to achieve sufficiently excellent water repellency and oil repellency.

As mentioned above, there has been a need for a technology that can impart water repellent and oil repellent functions to powders while improving their use feel and skin familiarity, and that can be produced at low cost.

SUMMARY OF THE INVENTION

Accordingly, it is one object of the present invention is to provide a technology that can impart water repellent and oil repellent functions to powders while improving the soft feel of the powders, and that can be produced at low cost.

This and other objects which will become apparent during the following detailed description, have been achieved by the inventors discovery that the above object can be achieved by producing $N^\varepsilon$-long chain acyl lysine crystals by a specific method.

Specifically, the present invention provides the following:
1) An $N^\varepsilon$-lauroyl lysine crystal or a mixture crystal of $N^\varepsilon$-octanoyl lysine and $N^\varepsilon$-lauroyl lysine, wherein a 90% particle diameter D90 of a number-based distribution is 2.8 μm or less.

(2) The $N^\varepsilon$-lauroyl lysine crystal or the mixture crystal of $N^\varepsilon$-octanoyl lysine and $N^\varepsilon$-lauroyl lysine according to (1), wherein a median diameter or average particle diameter of a volume-based distribution is 2.8 μm or less.

(3) An $N^\varepsilon$-lauroyl lysine crystal or a mixture crystal of $N^\varepsilon$-octanoyl lysine and $N^\varepsilon$-lauroyl lysine, wherein a bulk density is 0.34 g/mL or less.

(4) A non-grinding method of producing $N^\varepsilon$-long chain acyl lysine crystals comprising: preparing a solution in which at least one $N^\varepsilon$-long chain acyl lysine is dissolved in an acidic or basic solvent containing at least one selected from water-soluble organic solvents and/or water, and adding the solution dropwise to an acidic solution with a pH of 0.2 or higher and a pH lower than 2.0 at a temperature of 20° C. or lower, thereby crystallizing $N^\varepsilon$-long chain acyl lysine crystals.

(5) The $N^\varepsilon$-lauroyl lysine crystal or the mixture crystal of $N^\varepsilon$-octanoyl lysine and $N^\varepsilon$-lauroyl lysine according to any one of (1) to (3), which is obtained by the production method of (4).

(6) The $N^\varepsilon$-lauroyl lysine crystal or the mixture crystal of $N^\varepsilon$-octanoyl lysine and $N^\varepsilon$-lauroyl lysine according to any one of (1) to (5), wherein the crystal contains $N^\varepsilon$-octanoyl lysine at a ratio of 99 mass percent or less.

(7) A composition comprising: the $N^\varepsilon$-lauroyl lysine crystal or the mixture crystal of $N^\varepsilon$-octanoyl lysine and $N^\varepsilon$-lauroyl lysine according to any one of (1) to (3), (5), and (6) at 0.01 to 99.9 mass percent.

(8) A composition for industrial use comprising: the $N^\varepsilon$-lauroyl lysine crystal or the mixture crystal of $N^\varepsilon$-octanoyl lysine and $N^\varepsilon$-lauroyl lysine according to any one of (1) to (3), (5), and (6) at 0.01 to 99.9 mass percent.

(9) A cosmetic or a topical agent comprising: the $N^\varepsilon$-lauroyl lysine crystal or the mixture crystal of $N^\varepsilon$-octanoyl lysine and $N^\varepsilon$-lauroyl lysine according to any one of (1) to (3), (5), and (6) at 0.01 to 99.9 mass percent.

(10) A cleanser composition comprising: the $N^\varepsilon$-lauroyl lysine crystal or the mixture crystal of $N^\varepsilon$-octanoyl lysine and $N^\varepsilon$-lauroyl lysine according to any one of (1) to (3), (5), and (6) at 0.01 to 99.9 mass percent.

(11) A treated powder obtained by mixing a powder with the $N^\varepsilon$-lauroyl lysine crystal or the mixture crystal of $N^\varepsilon$-octanoyl lysine and $N^\varepsilon$-lauroyl lysine according to any one of (1) to (3), (5), and (6).

(12) The treated powder according to (11), wherein the powder includes crystalline or amorphous powders of resin powders, silicon-containing powders, metal oxides, carbon-containing powders, fluorine-containing powders, metallic salts, boron-containing powders, and composite powders.

(13) The treated powder according to (11) or (12), wherein of the $N^\varepsilon$-lauroyl lysine crystal coating a surface of the treated powder, a ratio of the $N^\varepsilon$-lauroyl lysine crystal with a particle diameter of 1.8 μm or less is 90% or more.

(14) The treated powder according to (11) or (12), wherein of the mixture crystal of $N^\varepsilon$-octanoyl lysine and $N^\varepsilon$-lauroyl lysine coating a surface of the treated powder, a ratio of the crystal with a particle diameter of 2.8 μm or less is 90% or more.

(15) A method of preparing the treated powder according to any one of (11) to (14), comprising: mixing a powder with the $N^\varepsilon$-lauroyl lysine crystal or the mixture crystal of $N^\varepsilon$-octanoyl lysine and $N^\varepsilon$-lauroyl lysine according to any one of (1) to (3), (5), and (6) at 5 mass percent, and coating 40% or more of a powder surface area with the $N^\varepsilon$-lauroyl lysine crystal or the mixture crystal of $N^\varepsilon$-octanoyl lysine and $N^\varepsilon$-lauroyl lysine.

(16) The method of preparation according to (15), wherein the mixing includes mixing by dry mixing that requires no solvent.

(17) The method of preparation according to (15) or (16), wherein the mixing includes mixing with a mixer for 60 minutes or less.

(18) The treated powder according to any one of (11) to (14) with water repellency.

(19) The treated powder according to any one of (11) to (14) and (18) with oil repellency.

(20) The treated powder according to any one of (11) to (14), (18), and (19) with a soft-focus effect.

(21) A composition comprising: the treated powder according to any one of (11) to (14) and (18) to (20) at 0.01 to 99.99 mass percent.

(22) The composition according to (21), which is a composition for industrial use, a cosmetic, a topical agent, or a cleanser.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 26 illustrates the evaluation results of water repellency and oil repellency for Example 3-22 to Example 3-26.

DETAILED DESCRIPTION OF THE PREFERRED EMBODIMENTS

Figure 1:
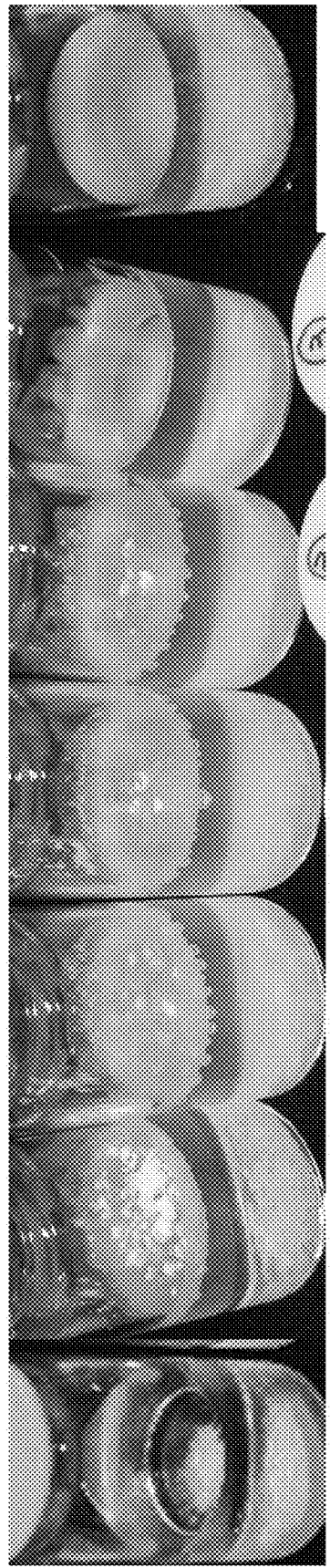
FIG. 1 illustrates the evaluation results of water repellency for Comparative Example 3-23, Example 3-1, Comparative Example 3-9, Comparative Example 3-16, Comparative Example 3-20, Comparative Example 3-1, and Comparative Example 3-21.
Figure 2:
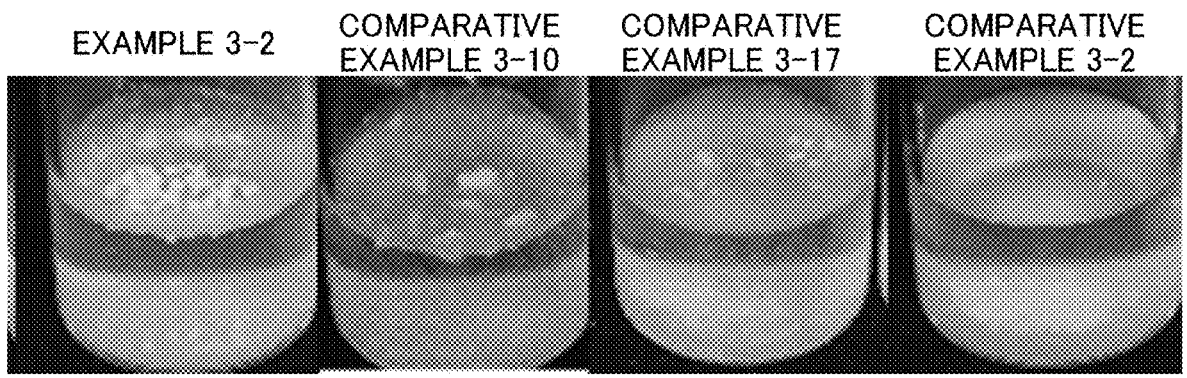
FIG. 2 illustrates the evaluation results of water repellency for Example 3-2, Comparative Example 3-10, Comparative Example 3-17, and Comparative Example 3-2.
Figure 3:
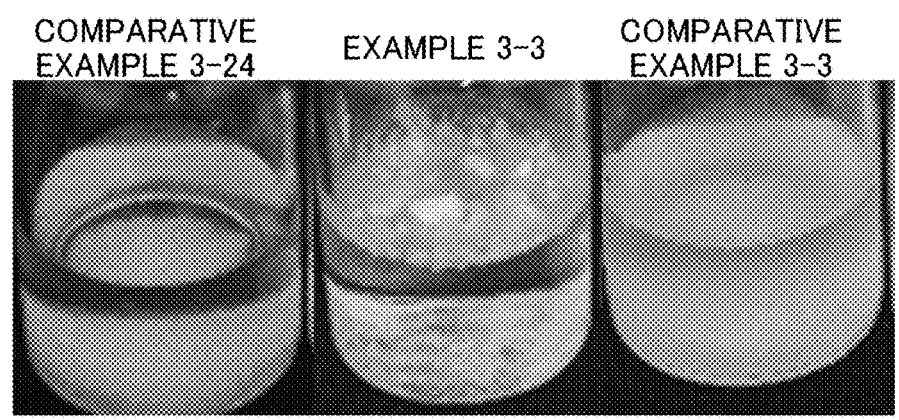
FIG. 3 illustrates the evaluation results of water repellency for Comparative Example 3-24, Example 3-3, and Comparative Example 3-3.
Figure 4:
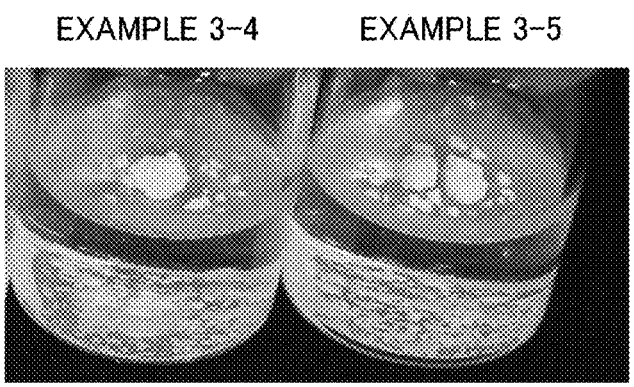
FIG. 4 illustrates the evaluation results of water repellency for Example 3-4 and Example 3-5.
Figure 5:
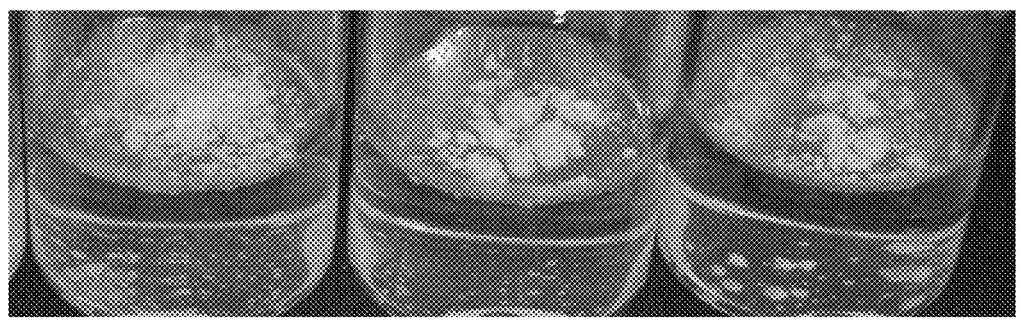
FIG. 5 illustrates the evaluation results of water repellency for Example 3-6, Example 3-7, and Example 3-8.
Figure 6:
FIG. 6 illustrates the evaluation results of water repellency for Comparative Example 3-25 and Example 3-9.
Figure 7:
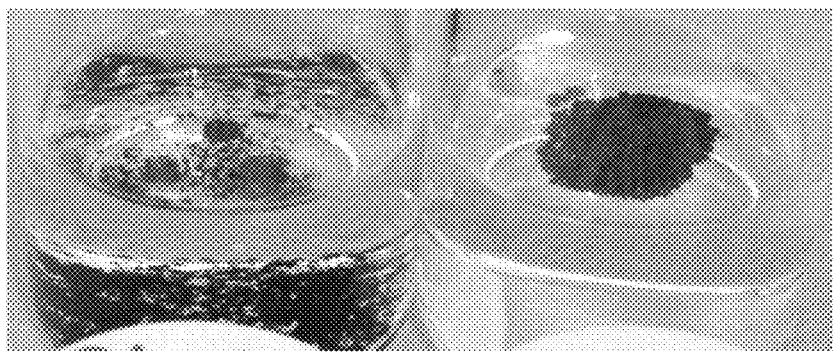
FIG. 7 illustrates the evaluation results of water repellency for Comparative Example 3-26 and Example 3-10.
Figure 8:
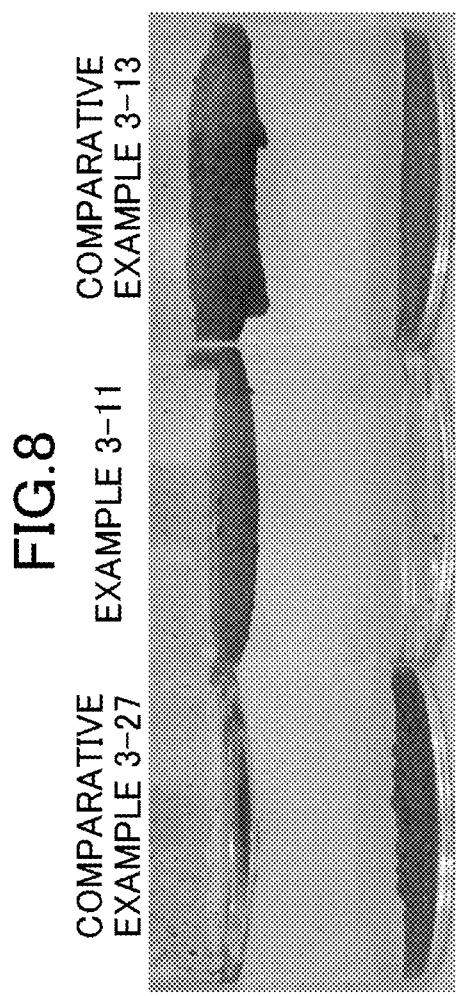
FIG. 8 illustrates the evaluation results of water repellency for Comparative Example 3-27, Example 3-11, and Comparative Example 3-13.
Figure 9:
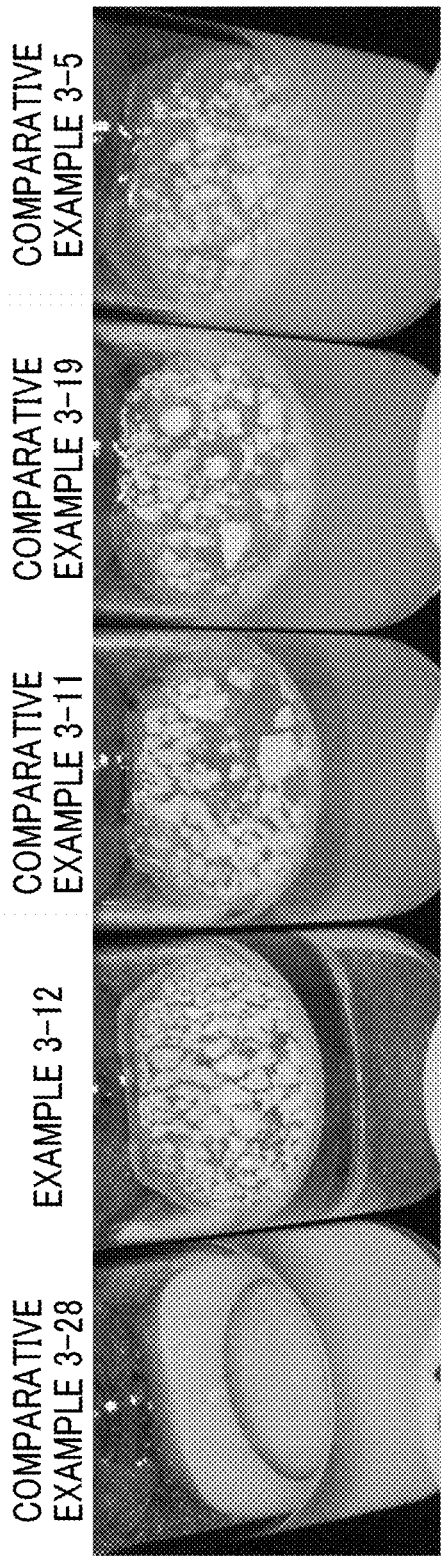
FIG. 9 illustrates the evaluation results of water repellency for Comparative Example 3-28, Example 3-12, Comparative Example 3-11, Comparative Example 3-19, and Comparative Example 3-5.
Figure 10:
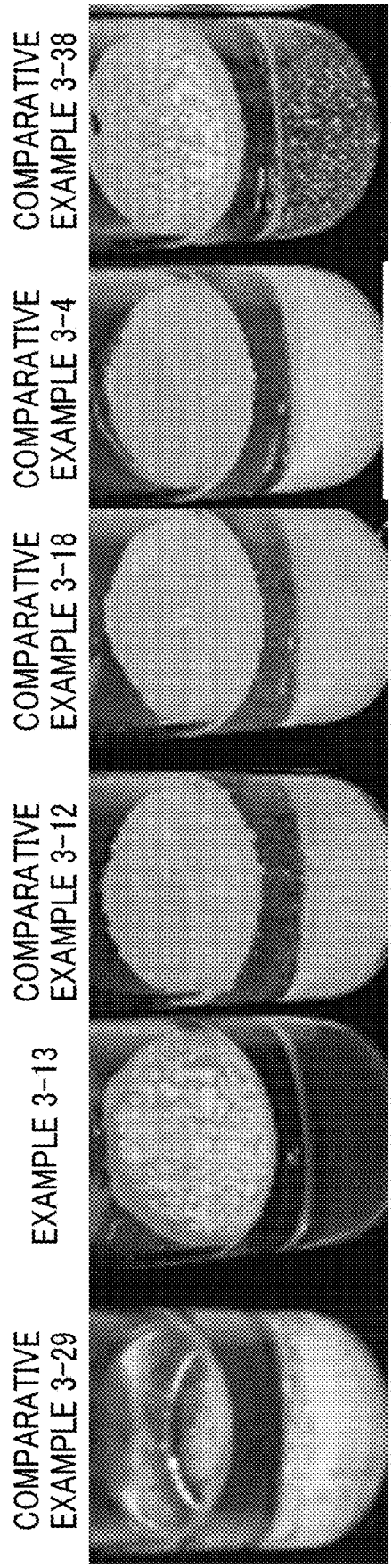
FIG. 10 illustrates the evaluation results of water repellency for Comparative Example 3-29, Example 3-13, Comparative Example 3-12, Comparative Example 3-18, Comparative Example 3-4, and Comparative Example 3-38.
Figure 11:
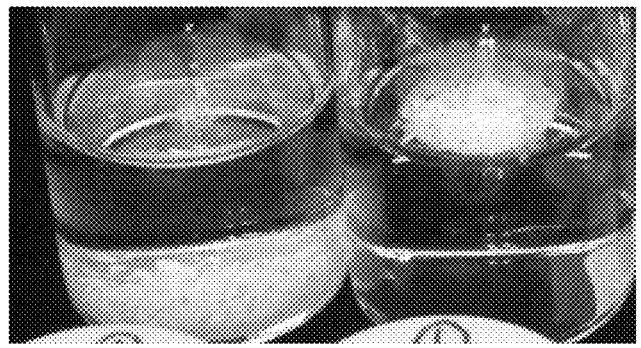
FIG. 11 illustrates the evaluation results of water repellency for Comparative Example 3-36 and Comparative Example 3-14.
Figure 12:
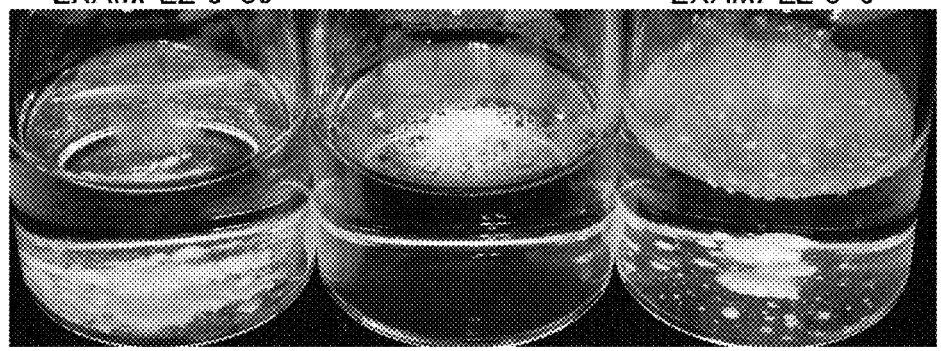
FIG. 12 illustrates the evaluation results of water repellency for Comparative Example 3-30, Example 3-15, and Comparative Example 3-6.
Figure 13:
FIG. 13 illustrates the evaluation results of water repellency for Comparative Example 3-31, Example 3-16, Comparative Example 3-15, and Comparative Example 3-7.
Figure 14:
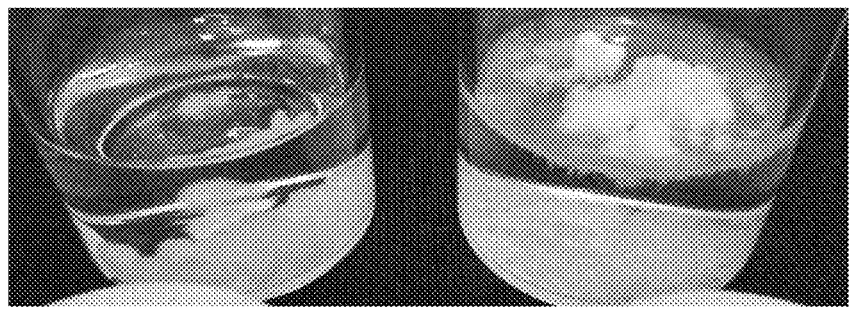
FIG. 14 illustrates the evaluation results of water repellency for Comparative Example 3-32 and Example 3-17.
Figure 15:
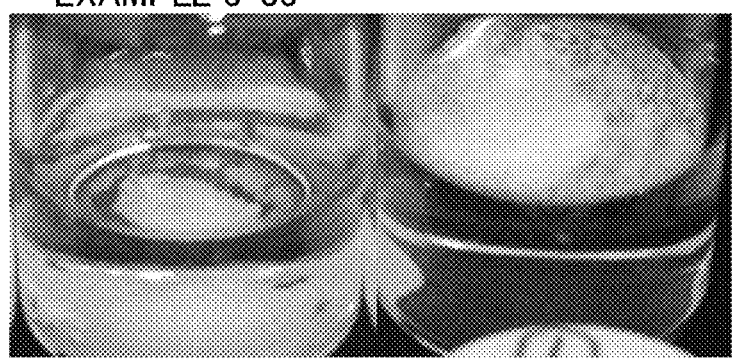
FIG. 15 illustrates the evaluation results of water repellency for Comparative Example 3-33 and Example 3-18.
Figure 16:
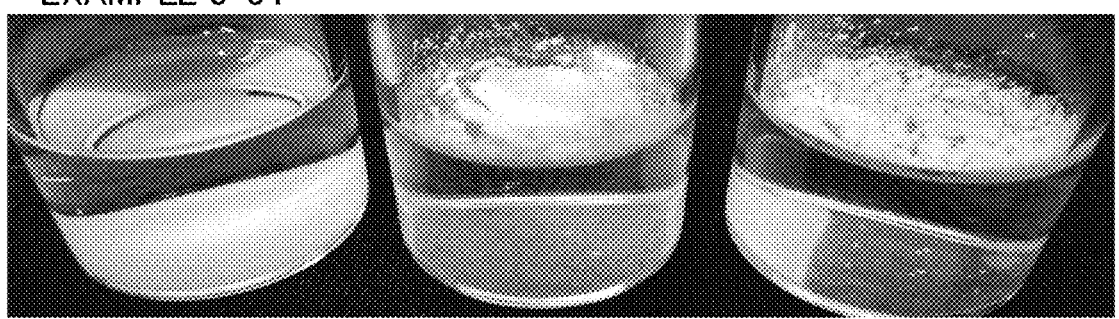
FIG. 16 illustrates the evaluation results of water repellency for Comparative Example 3-34, Example 3-19, and Example 3-20.
Figure 17:
FIG. 17 illustrates the evaluation results of water repellency for Comparative Example 3-35, Example 3-21, and Comparative Example 3-8.
Figure 18:
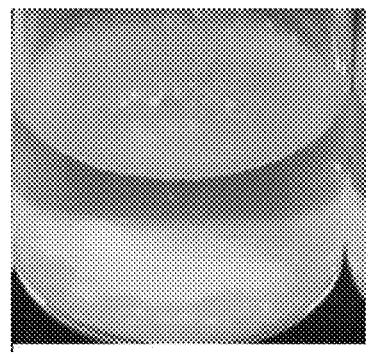
FIG. 18 illustrates the evaluation results of water repellency for Comparative Examples 3-37.
Figure 19:
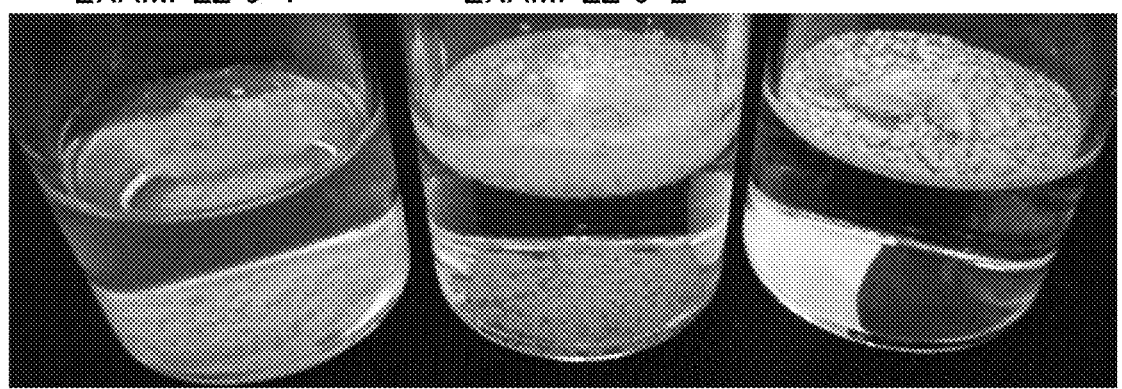
FIG. 19 illustrates the evaluation results of water repellency for Comparative Example 5-1, Comparative Example 5-2, and Example 5-1.
Figure 20:
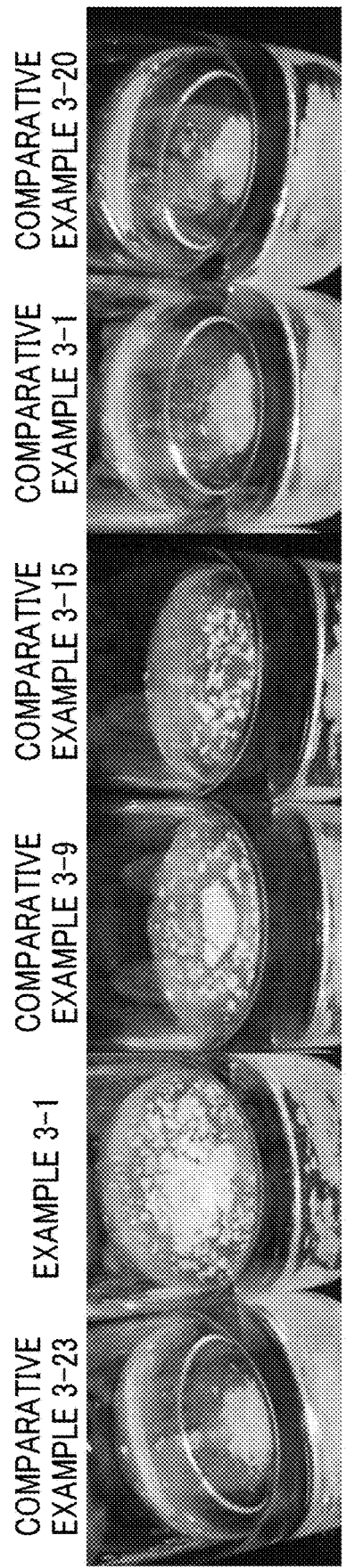
FIG. 20 illustrates the evaluation results of oil repellency for Comparative Example 3-23, Example 3-1, Comparative Example 3-9, Comparative Example 3-15, Comparative Example 3-1, and Comparative Example 3-20.
Figure 21:
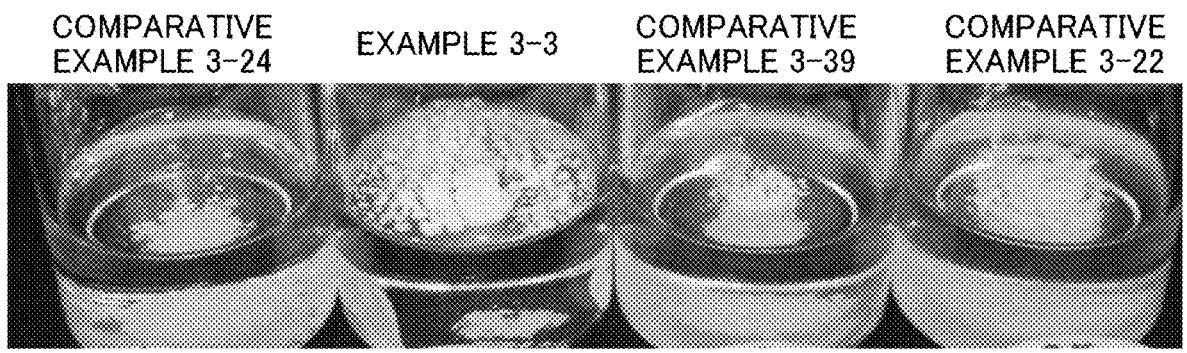
FIG. 21 illustrates the evaluation results of oil repellency for Comparative Example 3-24, Example 3-3, Comparative Example 3-39, and Comparative Example 3-22.
Figure 22:
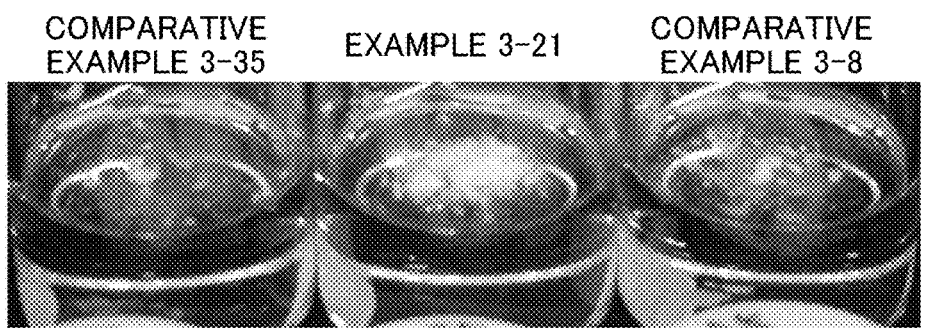
FIG. 22 illustrates the evaluation results of oil repellency for Comparative Example 3-35, Example 3-21, and Comparative Example 3-8.
Figure 23:
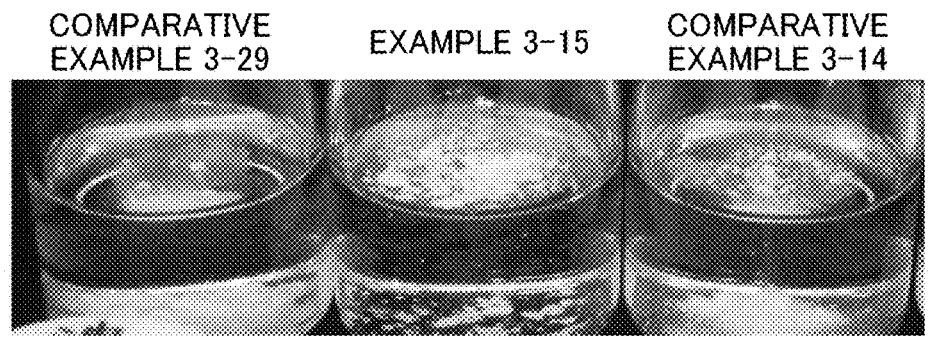
FIG. 23 illustrates the evaluation results of oil repellency for Comparative Example 3-29, Example 3-15, and Comparative Example 3-14.
Figure 24:
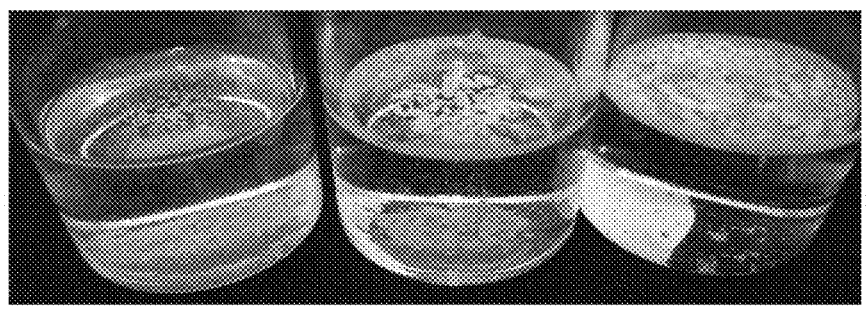
FIG. 24 illustrates the evaluation results of oil repellency for Comparative Example 5-1, Comparative Example 5-2, and Example 5-1.

The $N^\varepsilon$-long chain acyl lysine crystal production method of the present invention can be obtained in a non-grinding manner by a method including preparing a solution in which at least one $N^\varepsilon$-long chain acyl lysine is dissolved in an acidic or basic solvent containing at least one selected from water-soluble organic solvents and/or water, and adding the solution dropwise to an acidic solution with a pH of 0.2 or higher and a pH lower than 2.0 at a temperature of 20° C. or lower, thereby crystallizing $N^\varepsilon$-long chain acyl lysine crystals. The solution of $N^\varepsilon$-long chain acyl lysine can be obtained by dissolving crystals of $N^\varepsilon$-long chain acyl lysine, or by reacting fatty acids and lysine and using the reaction solution obtained without crystallization.

The long-chain acyl group of $N^\varepsilon$-long chain acyl lysine is a saturated or unsaturated fatty acid acyl having 8 to 22 carbon atoms, and examples thereof include octanoyl, lauroyl, myristoyl, palmitoyl, stearoyl, octyldodecyl, oleyl, behenyl, coconut oil fatty acid acyl, palm kernel oil fatty acid acyl, beef tallow fatty acid acyl, and the like, and lauroyl and octanoyl are preferable due to their general availability.

The water-soluble organic solvents include acetone, methanol, ethanol, propanol, butanol, isopropanol, and the like, with acetone, methanol, isopropanol, and butanol being preferable. These water-soluble organic solvents may be used alone, or two or more kinds may be mixed in combination.

When a water-soluble organic solvent and water are used in combination, the ratio is not particularly limited, and can be used in the range of water-soluble organic solvent/water=0/100 to 100/0 in a weight ratio, but preferably 55/45 to 70/30. When the weight ratio of both is less than 55/45 or greater than 70/30, the solubility of $N^\varepsilon$-long chain acyl lysine decreases and a large amount of solvent is required to dissolve $N^\varepsilon$-long chain acyl lysine, resulting in lower efficiency.

The acid used in the acidic solvent can be either an organic acid or an inorganic acid, and examples thereof include sulfuric acid, hydrochloric acid, nitric acid, phosphoric acid, citric acid, lactic acid, glutamic acid, and pyrrolidone carboxylic acid, and sulfuric acid and hydrochloric acid are preferable.

The base used in the basic solvent can be either an organic base or an inorganic base, examples thereof include sodium hydroxide, potassium hydroxide, calcium hydroxide, barium hydroxide, sodium carbonate, ammonia, triethylamine, triethanolamine, monoethanolamine, pyridine, arginine, lysine, and the like, and sodium hydroxide and potassium hydroxide are preferable.

The amount of acid or base in the acidic or basic solvent is not particularly limited, and may be a degree to which the $N^\varepsilon$-long chain acyl lysine can be dissolved.

The temperature during crystallization is not particularly limited as long as it is 20° C. or lower, but from the viewpoint that it is possible to obtain crystals with small median diameter and/or average particle diameter and/or 90% particle diameter D90 (number-based distribution), the temperature is preferably 15° C. or lower, further preferably 10° C. or lower, and particularly preferably 8° C. or lower. In addition, the lower limit of the temperature during crystallization may be the freezing point of the solvent or above.

The acidic solution used for crystallization can be prepared with the acids described above. The pH of the acidic solution is 0.2 or higher and lower than 2.0, preferably 0.7 to 1.3, and more preferably 0.8 to 1.1.

The crystals produced can be collected and dried by the commonly used methods.

The $N^\varepsilon$-long chain acyl lysine crystals thus obtained function as a stable pearlizing agent in the cleanser composition, and furthermore, when the skin and hair are washed with a cleanser composition containing such crystals, the conditioning effects of hair and skin are improved. In addition, when the crystals are contained in a cleanser composition, they can suppress the slimy feel of the cleanser during washing. Also, when used in an emulsion, the crystals can improve the moist feel and glossy feel of the emulsion.

In addition, by treating a powder with the crystals, it is possible to impart water repellent and oil repellent functions to the powder while improving the softness of the texture and shine of the powder when applied. The above crystals are preferably $N^\varepsilon$-lauroyl lysine crystals or mixture crystals of $N^\varepsilon$-octanoyl lysine and $N^\varepsilon$-lauroyl lysine. The mixture crystals of $N^\varepsilon$-octanoyl lysine and $N^\varepsilon$-lauroyl lysine can be a mixture of single crystals of $N^\varepsilon$-octanoyl lysine and $N^\varepsilon$-lauroyl lysine, or eutectic crystals of $N^\varepsilon$-octanoyl lysine and $N^\varepsilon$-lauroyl lysine. It is also preferable that the mixture crystals of $N^\varepsilon$-octanoyl lysine and $N^\varepsilon$-lauroyl lysine contain $N^\varepsilon$-octanoyl lysine in a ratio of 99 mass percent or less. The content of the $N^\varepsilon$-octanoyl lysine is more preferably 5 to 75%, further preferably 15 to 45%, and most preferably 20 to 30%.

In the $N^\varepsilon$-lauroyl lysine crystals, as well as the mixture crystals of $N^\varepsilon$-octanoyl lysine and $N^\varepsilon$-lauroyl lysine of the present invention, the 90% particle diameter D90 of the number-based distribution is 2.8 μm or less. The crystals of the present invention function as a stable pearlizing agent in the cleanser composition, and furthermore, when the skin and hair are washed with a cleanser composition containing such crystals, the conditioning effects of hair and skin are improved compared to $N^\varepsilon$-lauroyl lysine crystals and the like with a 90% particle diameter D90 of 3 μm or more. In addition, when the crystals of the present invention are contained in a cleanser composition, they can suppress the slimy feel of the cleanser during washing. Also, when used in an emulsion, the crystals of the present invention can improve the moist feel and glossy feel of the emulsion. In addition, by treating a powder with the crystals of the present invention, it is possible to impart water repellent and oil repellent functions to the powder while improving the softness of the texture and shine of the powder when applied.

The 90% particle diameter D90 is preferably 0.01 to 2.8 μm, more preferably 0.05 to 1 μm, and further preferably 0.1 to 0.7 μm.

In the $N^\varepsilon$-lauroyl lysine crystals, as well as the mixture crystals of $N^\varepsilon$-octanoyl lysine and $N^\varepsilon$-lauroyl lysine of the present invention, furthermore, the median diameter or average particle diameter of the volume-based distribution is 2.8 μm or less. The median diameter or the average particle diameter is preferably 0.01 to 2.8 μm, more preferably 0.05 to 2.0 μm, and further preferably 0.07 to 1.5 μm.

In addition, in another aspect, in the $N^\varepsilon$-lauroyl lysine crystals, as well as the mixture crystals of $N^\varepsilon$-octanoyl lysine and $N^\varepsilon$-lauroyl lysine of the present invention, the bulk density is 0.34 g/mL or less. The crystals of the present invention function as a stable pearlizing agent in the cleanser composition, and furthermore, when the skin and hair are washed with a cleanser composition containing such crystals, the conditioning effects of hair and skin are improved compared to $N^\varepsilon$-lauroyl lysine crystals and the like with a bulk density of 0.35 g/mL or more. In addition, when the crystals of the present invention are contained in a cleanser composition, they can suppress the slimy feel of the cleanser during washing. Also, when used in an emulsion, the crystals of the present invention can improve the moist feel and glossy feel of the emulsion. In addition, by treating a powder with the crystals of the present invention, it is possible to impart water repellent and oil repellent functions to the powder while improving the softness of the texture and shine of the powder when applied.

The bulk density is preferably 0.01 to 0.32 g/mL, more preferably 0.05 to 0.30 g/mL, and further preferably 0.1 to 0.25 g/mL.

In the $N^\varepsilon$-lauroyl lysine crystals or mixture crystals of $N^\varepsilon$-octanoyl lysine and $N^\varepsilon$-lauroyl lysine of the present invention, the median diameter, average particle diameter, and 90% particle diameter D90 can be determined by using a laser diffraction/scattering particle diameter distribution measurement device to measure the number-based or volume-based particle diameter distribution. The median diameter means the particle diameter at the point where the distribution curve of the cumulative percent passing % intersects the horizontal axis of 50%, and the 90% particle diameter D90 means the particle diameter at the point where the distribution curve of the cumulative percent passing % intersects the horizontal axis of 90%. The average particle diameter means the arithmetic mean particle diameter of the distribution. The "number-based distribution" represents a particle diameter distribution in which the number of particles is counted and this number is used as the basis for calculating the frequency of each particle diameter in the particle diameter distribution, and the "volume-based distribution" represents a particle diameter distribution in which the volume of particles assumed to be spherical is counted and this value is used as the basis for calculating the frequency of each particle diameter in the particle diameter distribution.

The present invention provides a composition containing the $N^\varepsilon$-lauroyl lysine crystals or mixture crystals of $N^\varepsilon$-octanoyl lysine and $N^\varepsilon$-lauroyl lysine at 0.01 to 99.9 mass percent. The composition of the present invention can be used as a composition for industrial use. For example, it can be blended into printing or writing inks, pencil leads, and the like to improve the color development, adhesion, and duration of pigments. Furthermore, it can be blended in paints from the viewpoint of preventing oxidation of pigments, improving water repellency, and improving dispersibility, and can also be blended in tires and paper. It can also be used as a lubricant for machinery.

The composition of the present invention can also be used as a cosmetic or a topical agent. The cosmetic or topical agent can be formulated in any form that can be applied to desired areas (such as skin, hair, scalp, lips, eye area, eyelashes, eyelids, and nails), for example, according to the usual methods. Cosmetics or topical agents for the skin, lips, eyelashes, and nails include, for example, suntan lotions such as sunscreens, body powders, and sprays, makeup cosmetics such as foundations, primers, body colors, bronzers, face powders, nail polishes, cheek colors, makeup bases, and concealers, lip cosmetics such as lip colors, lip liners, and lip sticks, eye makeup cosmetics such as eyeliners, eye shadows, eyebrows, and mascaras, leave-on cosmetics such as emulsions, lotions, creams, gels, and essences, and face masks. Cosmetics or topical agents for the hair include, for example, hairdressing agents, hair emulsions, hair treatments, hair conditioners, and hair lotions. Cosmetics or topical agents for the scalp include, for example, hair growth agents. Preferable cosmetics include, for example, makeup cosmetics, eye-makeup cosmetics, lip cosmetics, and leave-on cosmetics. Preferable topical agents include, for example, ointments, creams, mousses, and gels.

The composition of the present invention can be used as a cleanser composition. The cleanser composition is not particularly limited as long as it is a cleanser composition containing a surfactant, and the effects of the present invention are exhibited. More preferable examples include cleanser compositions such as facial cleansers, body soaps, soaps, cleansing balms, cleansing oils, and other skin cleansers, shampoos and other hair cleansers, dishwashing cleansers, vegetable cleansers, and machine cleansers.

The treated powder of the present invention can be obtained by mixing a powder with the $N^\varepsilon$-lauroyl lysine crystals or the mixture crystals of $N^\varepsilon$-octanoyl lysine and $N^\varepsilon$-lauroyl lysine. The powder is not particularly limited as long as it is used for industrial applications or cosmetics (pigments, dyes, resins, pearls), but examples thereof include resin powders such as nylon beads, silicone beads, and polyethylene beads;

metal oxides such as iron oxide (yellow pigment), iron oxide (red pigment), iron oxide (black pigment), tin oxide, chromium oxide, cobalt oxide, zinc oxide, pigment-grade zinc oxide, titanium dioxide, pigment-grade titanium dioxide, zirconium oxide, aluminum oxide, cerium oxide, fine particle titanium oxide, ultrafine particle titanium oxide, fine particle zinc oxide, and fine particle iron oxide;

silicone-containing powders such as silicates ((Al/Ca/Na) silicate, (Na/Mg) silicate, sericite, mica, talc, kaolin, bentonite, aluminum silicate, magnesium silicate, cubic Na aluminosilicate, silicon carbide, and silicon oxide including hydrous silica, and silicic anhydride (such as leaf-shaped silica, non-porous silica, porous silica, and semi-porous silica);

nylon powder, metallic fatty acid soaps such as Mg myristate, cellulose, cellulose particles, starch, wheat flour, wood powder, and carbon-containing powders such as carbon black, soot, ultramarine, Prussian blue, and carmine;

metallic salts such as barium sulfate, plate-shaped barium sulfate, butterfly state barium sulfate, calcium carbonate, and magnesium carbonate;

fluorine-containing powders such as synthetic gold mica (synthetic mica) and synthetic gold mica iron;

boron-containing powders such as boron nitride;

composite powders such as pearl powders, colored pearl pigments, and titanium mica; and waxes, dyes, rakes, and the like.

Moreover, the powder may be subjected to surface treatment such as silicone treatment, fluorine compound treatment, silane coupling agent treatment, silane treatment, organic titanate treatment, fatty acid treatment, metal soap treatment, oil agent treatment, and amino acid treatment. Note that crystalline or amorphous powders of resin powders, silicon-containing powders, metal oxides, carbon-containing powders, fluorine-containing powders, metallic salts, boron-containing powders, and composite powders are preferable in terms of improving water repellency and oil repellency after treatment.

The mixing of the powder with the $N^\varepsilon$-lauroyl lysine crystals or the mixture crystals of $N^\varepsilon$-octanoyl lysine and $N^\varepsilon$-lauroyl lysine can be carried out by mixing for 1 minute or more in a mixer. The mixing time is preferably 1 minute or more, and more preferably 10 minutes or more. The mixing time is preferably 60 minutes or less from the viewpoint of low-cost production without loss of productivity. As the mixer, it is possible to use high-speed agitating mixers such as Henschel mixers, household mixers, and high shear mixers, container rotary mixers or container rotary mixers with agitators such as W-type mixers, CV-type mixers, V-type mixers, and rocking mixers, mechanical agitating mixers such as ribbon agitating type, multi-shaft paddle type, double-shaft planetary agitating type, and conical screw type, airflow agitating mixers, compression, shear, and impact type mixers such as Julia mixers, Nauta mixers, and Nobilta, and the like, and high-speed agitating mixers are preferable from the viewpoint of inexpensive production and versatility.

The mixing may also be carried out by grinding the above powder and the $N^\varepsilon$-lauroyl lysine crystals or the mixture crystals of $N^\varepsilon$-octanoyl lysine and $N^\varepsilon$-lauroyl lysine. The above grinding can be carried out by grinding the above powder and the $N^\varepsilon$-lauroyl lysine crystals or the mixture crystals of $N^\varepsilon$-octanoyl lysine and $N^\varepsilon$-lauroyl lysine for at least 1 minute using a coarse grinder, medium grinder, grinder, or the like. The grinding time is preferably 1 minute or more, and more preferably 10 minutes or more. The mixing time is preferably 60 minutes or less from the viewpoint of low-cost production without loss of productivity. The coarse grinders that can be used include, for example, jaw crushers, the medium crushers include, for example, cutter mills, mortar machines, and the like, and the grinders include, for example, roller mills, jet mills, hammer mills, pin mills, rotary mills, attritors, bead mills, atomizers, and the like, but they are not limited to the above. For inexpensive production and versatility, jet mills, pin mills, rotary mills, atomizers, bead mills, and the like are preferable.

In the process of mixing the above powder with the $N^\varepsilon$-lauroyl lysine crystals or the mixture crystals of $N^\varepsilon$-octanoyl lysine and $N^\varepsilon$-lauroyl lysine, solvents with a boiling point of 130° C. or lower may be used in a mass percent of 10% or less of the total mixture, but it is preferable not to use them.

The treated powder contains the $N^\varepsilon$-lauroyl lysine crystals or the mixture crystals of $N^\varepsilon$-octanoyl lysine and $N^\varepsilon$-lauroyl lysine at 0.01 to 99.9 mass percent, preferably at 0.1 to 80 mass percent, and more preferably at 1 to 15 mass percent.

Of the $N^\varepsilon$-lauroyl lysine crystals coating the surface of the treated powder treated with $N^\varepsilon$-lauroyl lysine crystals, 90% or more of the crystals have a particle diameter of 1.8 μm or less, preferably 1.5 μm or less, and further preferably 1.2 μm or less.

In addition, of the mixture crystals of $N^\varepsilon$-octanoyl lysine and $N^\varepsilon$-lauroyl lysine coating the surface of the treated powder treated with mixture crystals of $N^\varepsilon$-octanoyl lysine and $N^\varepsilon$-lauroyl lysine, 90% or more of the crystals have a particle diameter of 2.8 μm or less, preferably 2.5 μm or less, and further preferably 1.8 μm or less.

As described above, powders treated with the $N^\varepsilon$-lauroyl lysine crystals or the mixture crystals of $N^\varepsilon$-octanoyl lysine and $N^\varepsilon$-lauroyl lysine of the present invention have water repellency. Also, powders treated with the $N^\varepsilon$-lauroyl lysine crystals or the mixture crystals of $N^\varepsilon$-octanoyl lysine and $N^\varepsilon$-lauroyl lysine of the present invention have oil repellency. In addition, powders treated with the $N^\varepsilon$-lauroyl lysine crystals or the mixture crystals of $N^\varepsilon$-octanoyl lysine and $N^\varepsilon$-lauroyl lysine of the present invention have a soft-focus effect.

The treated powder may be prepared by a method including mixing the powder with the $N^\varepsilon$-lauroyl lysine crystals or the mixture crystals of $N^\varepsilon$-octanoyl lysine and $N^\varepsilon$-lauroyl lysine at 5 mass percent, and coating 40% or more, preferably 50%, of a powder surface area with the $N^\varepsilon$-lauroyl lysine crystals or the mixture crystals of $N^\varepsilon$-octanoyl lysine and $N^\varepsilon$-lauroyl lysine. The coverage area ratio can be determined by image analysis using software such as ImageJ.

The mixing can be carried out by mixing for 1 minute or more in a mixer. The mixing time is preferably 1 minute or more, and more preferably 10 minutes or more. The mixing time is preferably 60 minutes or less from the viewpoint of low-cost production without loss of productivity. As the mixer, it is possible to use high-speed agitating mixers such as Henschel mixers, household mixers, and high shear mixers, container rotary mixers or container rotary mixers with agitators such as W-type mixers, CV-type mixers, V-type mixers, and rocking mixers, mechanical agitating mixers such as ribbon agitating type, multi-shaft paddle type, double-shaft planetary agitating type, and conical screw type, airflow agitating mixers, compression, shear, and impact type mixers such as Julia mixers, Nauta mixers, and Nobilta, and the like, and high-speed agitating mixers are preferable from the viewpoint of inexpensive production and versatility.

The mixing may also be carried out by grinding the above powder and the $N^\varepsilon$-lauroyl lysine crystals or the mixture crystals of $N^\varepsilon$-octanoyl lysine and $N^\varepsilon$-lauroyl lysine. The above grinding can be carried out by grinding the above powder and the $N^\varepsilon$-lauroyl lysine crystals or the mixture crystals of $N^\varepsilon$-octanoyl lysine and $N^\varepsilon$-lauroyl lysine for at least 1 minute using a coarse grinder, medium grinder, grinder, or the like. The grinding time is preferably 1 minute or more, and more preferably 10 minutes or more. The mixing time is preferably 60 minutes or less from the viewpoint of low-cost production without loss of productivity. The coarse grinders that can be used include, for example, jaw crushers, the medium crushers include, for example, cutter mills, mortar machines, and the like, and the grinders include, for example, roller mills, jet mills, hammer mills, pin mills, rotary mills, attritors, bead mills, atomizers, and the like, but they are not limited to the above. For inexpensive production and versatility, jet mills, pin mills, rotary mills, atomizers, bead mills, and the like are preferable.

In the mixing, solvents with a boiling point of 130° C. or lower may be used at a mass percent of 10% or less of the total treated powder, but it is preferable to use dry mixing, which does not require solvents, in order to reduce the environmental impact and allow easy, low-cost production.

The present invention provides a composition containing the treated powder at 0.01 to 99.9 mass percent. The composition of the present invention can be used as a composition for industrial use. For example, it can be blended into printing or writing inks, pencil leads, and the like to improve the color development, adhesion, and duration of pigments. Furthermore, it can be blended in paints from the viewpoint of preventing oxidation of pigments, improving water repellency, and improving dispersibility, and can also be blended in tires and paper. It can also be used as a lubricant for machinery.

The composition of the present invention can also be used as a cosmetic or a topical agent. The cosmetic or topical agent can be formulated in any form that can be applied to desired areas (such as skin, hair, scalp, lips, eye area, eyelashes, eyelids, and nails), for example, according to the usual methods. Cosmetics or topical agents for the skin, lips, eyelashes, and nails include, for example, suntan lotions such as sunscreens, body powders, and sprays, makeup cosmetics such as foundations, primers, body colors, bronzers, face powders, nail polishes, cheek colors, makeup bases, and concealers, lip cosmetics such as lip colors, lip liners, and lip sticks, eye makeup cosmetics such as eyeliners, eye shadows, eyebrows, and mascaras, leave-on cosmetics such as emulsions, lotions, creams, gels, and essences, and face masks. Cosmetics or topical agents for the hair include, for example, hairdressing agents, hair emulsions, hair treatments, hair conditioners, and hair lotions. Cosmetics or topical agents for the scalp include, for example, hair growth agents. Preferable cosmetics include, for example, makeup cosmetics, eye-makeup cosmetics, lip cosmetics, and leave-on cosmetics. Preferable topical agents include, for example, ointments, creams, mousses, and gels.

The composition of the present invention can be used as a cleanser composition. The cleanser composition is not particularly limited as long as it is a cleanser composition containing a surfactant, and the effects of the present invention are exhibited. More preferable examples include cleanser compositions such as facial cleansers, body soaps, soaps, cleansing balms, cleansing oils, and other skin cleansers, shampoos and other hair cleansers, dishwashing cleansers, vegetable cleansers, and machine cleansers.

The crystals or treated powder of the present invention can be combined with preservatives such as caprylyl glycol, glyceryl caprylate, phenoxyethanol, chlorphenesin, pentylene glycol, hexylene glycol, methylparaben, and propylparaben; antioxidants such as tocopherol, vitamin C, and BHT; chelating agents such as Na ethylenediaminetetraacetate; binders such as ethyl cellulose and hydroxypropyl cellulose; thickening agents such as xanthan gum, carbomer, and polyacrylate crosspolymer; oil gelling agents such as dibutyl ethylhexanoyl glutamide, dibutyl lauroyl glutamide, dextrin palmitate, and polyamide-3; moisturizers such as glycerin and 1,3-butylene glycol; emulsifiers such as polyoxyethylene-based or polysorbate-based emulsifiers, fatty acid polyglyceryl, and sorbitan fatty acid esters; and oil agents such as ester oils and hydrocarbon oils, as long as these effects are not impaired.

Other features of the invention will become apparent in the course of the following descriptions of exemplary embodiments which are given for illustration of the invention and are not intended to be limiting thereof.

EXAMPLES

Particle Size Distribution and Particle Diameter Measurement Methods;

A laser diffraction/scattering particle diameter distribution measurement device (Partica LA-950, manufactured by HORIBA) was used to measure the particle diameter distribution using cumulative volume values. The results obtained from the measurement were analyzed using the software provided to the device to obtain the various particle diameters of the number-based distribution and volume-based distribution. To 5 g of isopropyl alcohol, 20 mg of the $N^\varepsilon$-lauroyl lysine crystals or the mixture crystals of $N^\varepsilon$-octanoyl lysine and $N^\varepsilon$-lauroyl lysine was added and exposed to ultrasound with agitation for 30 minutes using an ultrasonic device with an output of Watt to crush and disperse the crystals. An appropriate amount of this dispersion was added to 500 mL of isopropyl alcohol according to the device procedures, and a dispersion sample of moderate concentration was adjusted while checking the transparency. This sample was circulated at a flow rate of 10 mL/min and ultrasonicated for 30 minutes to disperse it to primary particles, followed by degassing to determine the particle size distribution and various particle diameters of $N^\varepsilon$-lauroyl lysine crystals in the sample using a flow cell.

Bulk Density Measurement Method:

$N^\varepsilon$-lauroyl lysine crystals or the mixture crystals of $N^\varepsilon$-octanoyl lysine and $N^\varepsilon$-lauroyl lysine were crushed by agitation with a mixer for 2 minutes or more. The bulk density of the obtained crystals was measured using Powder Rheometer FT-4 (manufactured by Freeman Technology™). Specifically, a fixed amount of the $N^\varepsilon$-lauroyl lysine crystals or the mixture crystals of $N^\varepsilon$-octanoyl lysine and $N^\varepsilon$-lauroyl lysine were measured into a holder and then conditioned according to the utilization procedures. The bulk density was measured from the volume after conditioning and the mass of the $N^\varepsilon$-lauroyl lysine crystals or the mixture crystals of $N^\varepsilon$-octanoyl lysine and $N^\varepsilon$-lauroyl lysine using the following formula.

Bulk Density=Mass after Conditioning/Volume after Conditioning (g/mL)

Preparation of Fine Powder $N^\varepsilon$-Lauroyl Lysine Crystals by Grinding Method Comparative Example 1-1

$N^\varepsilon$-lauroyl lysine crystals with a 90% particle diameter D90 (number-based distribution) of 15.7 μm were ground using a dry grinding method under alcohol-free conditions as follows.

To 100 parts by weight of $N^\varepsilon$-lauroyl lysine crystals, 16 parts by weight of water were added and mixed, and then the mixture was fed into a dry bead mill (manufactured by Ashizawa Finetech Ltd., model SDA-120) at a rate of 0.5 kg/h for grinding. The beads used were beads made of partially stabilized zirconia (PSZ) (1.5 mm in diameter), and the bead filling ratio was 70% (v/v) of the volume. The powder obtained after grinding was dried and crushed in a mixer to obtain the desired fine powder $N^\varepsilon$-lauroyl lysine crystals. Table 1 presents the bulk densities and various particle diameters of the obtained crystals.

Comparative Example 1-2

$N^\varepsilon$-lauroyl lysine crystals with a 90% particle diameter D90 (number-based distribution) of 15.7 μm were ground using a dry grinding method under solvent-present conditions as follows.

To 100 parts by weight of $N^\varepsilon$-lauroyl lysine crystals, 1 part by weight of ethanol were added and mixed, and then the mixture was fed into a dry bead mill (manufactured by Ashizawa Finetech Ltd., model SDA-120) at a rate of 0.5 kg/h for grinding. The beads used were beads made of partially stabilized zirconia (PSZ) (1.5 mm in diameter), and the bead filling ratio was 70% (v/v) of the volume. The powder obtained after grinding was dried and crushed in a high-speed mixer to obtain the desired fine powder $N^\varepsilon$-lauroyl lysine crystals. Table 1 presents the bulk densities and various particle diameters of the obtained crystals.

Comparative Example 1-3

$N^\varepsilon$-lauroyl lysine crystals with a 90% particle diameter D90 (number-based distribution) of 15.7 μm were ground using a wet grinding method under alcohol-present conditions as follows.

$N^\varepsilon$-lauroyl lysine was ground according to the Examples in Japanese Patent Application Publication No. Hei 09-323914, which is incorporated herein by reference in its entirety. The powder obtained after grinding was dried and crushed with a high-speed mixer to obtain the desired fine powder $N^\varepsilon$-lauroyl lysine crystals. Table 1 presents the bulk densities and various particle diameters of the obtained crystals.

Comparative Example 1-4

$N^\varepsilon$-lauroyl lysine crystals with a 90% particle diameter D90 (number-based distribution) of 15.7 μm were ground using a dry grinding method under alcohol-free and water-free conditions as follows.

$N^\varepsilon$-lauroyl lysine was ground according to the Production Comparative Example 4 described in Japanese Patent No. 4826049, which is incorporated herein by reference in its entirety, to obtain fine powder $N^\varepsilon$-lauroyl lysine crystals. Table 1 presents the bulk densities and various particle diameters of the obtained crystals.

The particle diameters and physical properties of the fine powder $N^\varepsilon$-lauroyl lysine crystals obtained in Comparative Examples 1-1 to 1-4 are summarized in Table 1.

TABLE 1

Particle diameter and physical properties of fine powder $N^\varepsilon$-Mauroyl lysine crystals

| Grinding Condition | Comparative Example 1-1 | Comparative Example 1-2 | Comparative Example 1-3 | Comparative Example 1-4 |
|---|---|---|---|---|
| Grinder Used and Grinding Method | Dry Bead Mill | Dry Bead Mill | Wet Bead Mill | Jet Mill |
| Mass Percent of Alcohol/Mass Percent of $N^\varepsilon$-Lauroyl Lysine | 0 | 0.01 | 10 | 0 |
| Mass Percent of Water/Mass Percent of $N^\varepsilon$-Lauroyl Lysine | 0.16 | 0 | 0 | 0 |
| Grinding Count | 1 | 1 | 20 | — |
| 90% Particle Diameter D90 (Number-Based Distribution) μm | 6.30 | 6.80 | 3.60 | 8.80 |
| Average Particle Diameter (Number-Based Distribution) μm | 3.80 | 3.90 | 2.90 | 4.30 |
| Average Particle Diameter (Volume-Based Distribution) μm | 6.40 | 8.40 | 3.50 | 9.00 |
| Median Diameter (Volume-Based Distribution) μm | 6.10 | 8.50 | 3.40 | 8.90 |
| Bulk Density g/mL | 0.37 | 0.39 | 0.35 | 0.40 |

Preparation of fine powder $N^\varepsilon$-lauroyl lysine crystals or mixture crystals of $N^\varepsilon$-octanoyl lysine and $N^\varepsilon$-lauroyl lysine by crystallization method]

Example 2-1

In a mixed solution of 97.4 g of methanol and 62.7 g of water, 5.7 g of sodium hydroxide was dissolved at room temperature, followed by heating to about 50° C., and then 36.4 g of commercially available $N^\varepsilon$-lauroyl lysine crystals was added and dissolved at the same temperature.

After that, a solution of $N^\varepsilon$-lauroyl lysine was added dropwise over 75 minutes to an aqueous hydrochloric acid solution (600 mL) with a concentration of 0.1 mol/L, which had been kept cooled 10° C. or lower, while maintaining the pH at 0.7 to 1.3.

After the dropwise addition was completed, the pH was adjusted to 7.0 with sodium hydroxide, and the precipitated crystals were filtered and dried under reduced pressure to obtain 36.0 g of white crystals.

The obtained white crystals were dried and crushed with a high-speed mixer to obtain the desired fine powder $N^\varepsilon$-lauroyl lysine crystals. Table 2-1 presents the bulk densities and various particle diameters of the obtained crystals.

Example 2-2

In a mixed solution of 97.4 g of methanol and 62.7 g of water, 5.7 g of sodium hydroxide was dissolved at room temperature, followed by heating to about 50° C., and then 36.4 g of commercially available $N^\varepsilon$-lauroyl lysine crystals was added and dissolved at the same temperature.

After that, a solution of $N^\varepsilon$-lauroyl lysine was added dropwise over 25 minutes to an aqueous hydrochloric acid solution (150 mL) with a concentration of 0.085 mol/L, which had been kept cooled 0° C. or lower, while maintaining the pH at 0.8 to 1.1.

After the dropwise addition was completed, the pH was adjusted to 7.0 with sodium hydroxide, and the precipitated crystals were filtered and dried under reduced pressure to obtain 36.0 g of white crystals.

The obtained white crystals were dried and crushed with a high-speed mixer to obtain the desired fine powder $N^\varepsilon$-lauroyl lysine crystals. Table 2-1 presents the bulk densities and various particle diameters of the obtained crystals.

Example 2-3

Mixture crystals of $N^\varepsilon$-octanoyl lysine and $N^\varepsilon$-lauroyl lysine (1:1) were obtained according to the method of Example 2-2 except that commercially available $N^\varepsilon$-octanoyl lysine crystals and $N^\varepsilon$-lauroyl lysine crystals were used at a ratio of 1:1 instead of commercially available $N^\varepsilon$-lauroyl lysine crystals. Table 2-2 presents the bulk densities and various particle diameters of the obtained mixed bodies.

Example 2-4

Mixture crystals of $N^\varepsilon$-octanoyl lysine and $N^\varepsilon$-lauroyl lysine (1:3) were obtained according to the method of Example 2-2 except that commercially available $N^\varepsilon$-octanoyl lysine crystals and $N^\varepsilon$-lauroyl lysine crystals were used at a ratio of 1:3 instead of commercially available $N^\varepsilon$-lauroyl lysine crystals. Table 2-2 presents the bulk densities and various particle diameters of the obtained mixed bodies.

Example 2-5

Mixture crystals of $N^\varepsilon$-octanoyl lysine and $N^\varepsilon$-lauroyl lysine (1:9) were obtained according to the method of Example 2-2 except that commercially available $N^\varepsilon$-octanoyl lysine crystals and $N^\varepsilon$-lauroyl lysine crystals were used at a ratio of 1:9 instead of commercially available $N^\varepsilon$-lauroyl lysine crystals. Table 2-2 presents the bulk densities and various particle diameters of the obtained mixed bodies.

Example 2-6

Mixture crystals of $N^\varepsilon$-octanoyl lysine and $N^\varepsilon$-lauroyl lysine (3:1) were obtained according to the method of Example 2-2 except that commercially available $N^\varepsilon$-octanoyl lysine crystals and $N^\varepsilon$-lauroyl lysine crystals were used at a ratio of 3:1 instead of commercially available $N^\varepsilon$-lauroyl lysine crystals. Table 2-2 presents the bulk densities and various particle diameters of the obtained mixed bodies.

Comparative Example 2-1

In 150 ml of 10% aqueous sodium hydroxide solution, 30 g of $N^\varepsilon$-lauroyl lysine was dissolved according to the Production Example 1 described in Japanese Patent Application Publication No. Hei 8-337519.

The obtained solution of $N^\varepsilon$-lauroyl lysine was added dropwise to 200 ml of 2 mol/L aqueous hydrochloric acid solution at room temperature with agitation, maintaining the pH at 2 to 5.

After dropwise addition of the entire amount, the pH was adjusted to 7.0 with sodium hydroxide, and the precipitated crystals were filtered and dried to obtain 29.6 g of white crystals.

The obtained white crystals were dried and crushed with a high-speed mixer to obtain the desired fine powder $N^\varepsilon$-lauroyl lysine crystals. Table 2-1 presents the bulk densities and various particle diameters of the obtained crystals.

Comparative Example 2-2

In a mixed solution of 97.4 g of methanol and 62.7 g of water, 5.7 g of sodium hydroxide was dissolved at room temperature, followed by heating to about 50° C., and then 36.4 g of $N^\varepsilon$-lauroyl lysine was added and dissolved at the same temperature, according to Production Example 2 described in Japanese Patent No. 4826049.

The solution was then cooled to 25° C., and 38.0 g of 17.5% hydrochloric acid was added dropwise over about 4 hours at the same temperature with agitation, maintaining the pH at 7 to 12.

After dropwise addition of the entire amount, the pH was adjusted to 7.0 with hydrochloric acid, and the precipitated crystals were filtered and dried to obtain 35.0 g of white crystals.

The obtained white crystals were dried and crushed with a high-speed mixer to obtain the desired fine powder $N^\varepsilon$-lauroyl lysine crystals. Table 2-1 presents the bulk densities and various particle diameters of the obtained crystals.

Comparative Example 2-3

In a mixed solution of 97.4 g of methanol and 62.7 g of water, 5.7 g of sodium hydroxide was dissolved at room temperature, followed by heating to about 50° C., and then 36.4 g of $N^\varepsilon$-lauroyl lysine was added and dissolved at the same temperature.

After that, a solution of $N^\varepsilon$-lauroyl lysine was added dropwise over 25 minutes to an aqueous hydrochloric acid solution (150 mL) with a concentration of 1.01 mol/L, which had been kept under control at 25° C., without controlling the pH of the reaction system.

After the dropwise addition was completed, the pH was adjusted to 7.0 with sodium hydroxide, and the precipitated crystals were filtered and dried under reduced pressure to obtain 35.8 g of white crystals.

The obtained white crystals were dried and crushed with a high-speed mixer to obtain the desired fine powder $N^\varepsilon$-lauroyl lysine crystals. Table 2-1 presents the bulk densities and various particle diameters of the obtained crystals.

Comparative Example 2-4

In a mixed solution of 97.4 g of methanol and 62.7 g of water, 5.7 g of sodium hydroxide was dissolved at room temperature, followed by heating to about 50° C., and then 36.4 g of $N^\varepsilon$-lauroyl lysine was added and dissolved at the same temperature.

After that, a solution of $N^\varepsilon$-lauroyl lysine was added dropwise over 25 minutes to an aqueous hydrochloric acid solution (150 mL) with a concentration of 1.01 mol/L, which had been kept under control at 5° C., without controlling the pH of the reaction system.

After the dropwise addition was completed, the pH was adjusted to 7.0 with sodium hydroxide, and the precipitated crystals were filtered and dried under reduced pressure to obtain 34.9 g of white crystals.

The obtained white crystals were dried and crushed with a high-speed mixer to obtain the desired fine powder $N^\varepsilon$-lauroyl lysine crystals. Table 2-1 presents the bulk densities and various particle diameters of the obtained crystals.

Tables 2-1 and 2-2 present the particle diameters and physical properties of the $N^\varepsilon$-lauroyl lysine crystals, $N^\varepsilon$-octanoyl lysine crystals, and mixture crystal of $N^\delta$-octanoyl lysine and $N^\varepsilon$-lauroyl lysine obtained in Examples 2-1 to 2-6, and Comparative Examples 2-1 to 2-4.

TABLE 2-1

Particle diameter and physical properties of fine powder $N^\varepsilon$-lauroyl lysine crystals

| Crystallization Condition | Example 2-1 | Example 2-2 | Comparative Example 2-1 | Comparative Example 2-2 | Comparative Example 2-3 | Comparative Example 2-4 |
|---|---|---|---|---|---|---|
| Falling-Drop Method | Basic Solution in Acid | Basic Solution in Acid | Basic Solution in Acid | Acid in Basic Solution | Basic Solution in Acid | Basic Solution in Acid |
| Initial acid concentration in acidic solution used to neutralize and crystallize basic solution of $N^\varepsilon$-lauroyl lysine mol/L | 0.1 | 0.085 | 2 | 6 | 1.01 | 1.01 |
| pH Control Range Required to Obtain Desired Particle Diameter during Neutralization Crystallization Reaction | 0.7 to 1.3 | 0.8 to 1.1 | 2 to 5 | 7 to 12 | pH Range Not Controlled | 2 to 5 |
| Temperature during Neutralization Crystallization Step (° C.) | 10 | 0 | 25 | 10 | 25 | 5 |
| 90% Particle Diameter D90 (Number-Based Distribution) μm | 0.20 | 0.20 | 17.20 | 6.70 | 15.60 | 10.00 |
| Average Particle Diameter (Number-Based Distribution) μm | 0.18 | 0.12 | 9.80 | 3.60 | 8.80 | 7.20 |

TABLE 2-1-continued

Particle diameter and physical properties of fine powder $N^\varepsilon$-lauroyl lysine crystals

| Crystallization Condition | Example 2-1 | Example 2-2 | Comparative Example 2-1 | Comparative Example 2-2 | Comparative Example 2-3 | Comparative Example 2-4 |
|---|---|---|---|---|---|---|
| Average Particle Diameter (Volume-Based Distribution) μm | 1.80 | 0.37 | 18.00 | 6.20 | 16.10 | 11.60 |
| Median Diameter (Volume-Based Distribution) μm | 1.50 | 0.37 | 17.80 | 6.00 | 16.00 | 10.40 |
| Bulk Density g/mL | 0.18 | 0.14 | 0.42 | 0.38 | 0.42 | 0.40 |

TABLE 2-2

Particle diameter and physical properties of mixture crystals of $N^\varepsilon$-octanoyl lysine and $N^\varepsilon$-lauroyl lysine

| Crystallization Condition | Example 2-3 | Example 2-4 | Example 2-5 | Example 2-6 |
|---|---|---|---|---|
| Falling-Drop Method | Basic Solution in Acid | Basic Solution in Acid | Basic Solution in Acid | Basic Solution in Acid |
| Initial Acid Concentration in Acidic Solution Used for Neutralization Crystallization mol/L | 0.085 | 0.085 | 0.085 | 0.085 |
| pH Control Range Required to Obtain Desired Particle Diameter during Neutralization Crystallization Reaction | 0.8 to 1.1 | 0.8 to 1.1 | 0.8 to 1.1 | 0.8 to 1.1 |
| Temperature during Neutralization Crystallization Step (° C.) | 0 | 0 | 0 | 0 |
| 90% Particle Diameter D90 (Number-Based Distribution) μm | 0.42 | 0.42 | 0.42 | 0.42 |
| Average Particle Diameter (Number-Based Distribution) μm | 0.30 | 0.30 | 0.30 | 0.30 |
| Average Particle Diameter (Volume-Based Distribution) μm | 3.60 | 2.70 | 2.10 | 4.20 |
| Median Diameter (Volume-Based Distribution) μm | 2.30 | 0.86 | 0.67 | 3.90 |
| Bulk Density g/mL | 0.22 | 0.17 | 0.16 | |

Example 3

The powders were treated in the ratios and methods presented in Tables 5-1 to 5-4, and the water repellency and oil repellency of the treated powders were evaluated.

FIGS. 1 to 19 present the results of water repellency evaluation, and FIGS. 20 to 24 present the results of oil repellency evaluation.

Water Repellency Evaluation:

The solvent in an amount of 5 g was measured in a vial, and 30 mg of untreated powder or various treated powder was added to the surface of the solvent from a height of 3 cm within 2 seconds. After the addition, the mixture was allowed to stand for 60 minutes, and the amount of powder floating on the solvent was determined visually and by image analysis using ImageJ. It can be judged that the larger the amount of powder floating on the solvent, the more efficiently the surface of the powder was coated with the $N^\varepsilon$-lauroyl lysine crystals or the mixture crystals of $N^\varepsilon$-octanoyl lysine and $N^6$-lauroyl lysine, so that the surface of the powder is hard to wet with the solvent, meaning high water repellency.

The solvents used to evaluate the water repellency of the various powders were prepared according to the properties of the surface of the powder as presented in Table 3.

TABLE 3

Solvents used to evaluate water repellency of various powder

| | Water (Mass Percent) | Ethanol (Mass Percent) |
|---|---|---|
| Plate-Shaped Silicate | 70 | 30 |
| Spherical or Rod-Shaped Metal Oxide | 90 | 10 |
| Plate-Shaped Metal Oxide | 90 | 10 |

TABLE 3-continued

Solvents used to evaluate water repellency of various powder

| | Water (Mass Percent) | Ethanol (Mass Percent) |
|---|---|---|
| Carbon-Containing Powder | 90 | 10 |
| Silica Anhydride, Hydrous Silica, Bentonite | 100 | 0 |

Oil Repellency Evaluation:

A liquid pseudo-sebum was prepared by uniformly mixing oils similar to the compositions of sebum in the ratios presented in Table 4. This pseudo-sebum in an amount of 5 g was measured in a vial, and 30 mg of untreated powder or various treated powder was added to the surface of the liquid sebum from a height of 3 cm within 2 seconds. After the addition, the mixture was allowed to stand for a certain period of time, and the amount of powder floating on the liquid sebum was determined visually and by image analysis using ImageJ. It can be judged that the larger the amount of powder floating on the liquid sebum, the more efficiently the surface of the powder was coated with the $N^\varepsilon$-lauroyl lysine crystals or the mixture crystals of $N^\varepsilon$-octanoyl lysine and $N^\varepsilon$-lauroyl lysine, so that the surface of the powder is hard to wet with the liquid sebum, meaning high oil repellency.

TABLE 4

| Oil | Mass Percent |
|---|---|
| Glyceryl Tri(Caprylate/Caprate) | 33.3 |
| Octyldodecanol Myristate | 33.3 |
| Oleic Acid | 20 |
| Squalane | 13.4 |

TABLE 5-1

Details on method of treating various powders with Nε-lauroyl lysine crystals

| | | | | Treatment of Powder by Simple Mixing Method | | | |
|---|---|---|---|---|---|---|---|
| | Powder Type | Rotating Speed of Mixer Blades m/s | Mixing Time (Min) | Mass percent of commercially available $N^\varepsilon$-lauroyl lysine crystals (D90 = 15.7 μm) relative to 100 mass percent of powder (%) | Mass percent of $N^\varepsilon$-lauroyl lysine crystals of Comparative Example 1-3 relative to 100 mass percent of powder (%) | Mass percent of $N^\varepsilon$-lauroyl lysine crystals of Comparative Example 2-2 relative to 100 mass percent of powder (%) | Mass percent of $N^\varepsilon$-lauroyl lysine crystals of Comparative Example 2-4 relative to 100 mass percent of powder (%) |
| Comparative Example 3-1 | Talc | 40 | 10 | 5 | | | |
| Comparative Example 3-2 | Talc | 40 | 10 | 3 | | | |
| Comparative Example 3-3 | Sericite | 40 | 10 | 3 | | | |
| Comparative Example 3-4 | Pigment-Grade Titanium Oxide | 40 | 10 | 5 | | | |
| Comparative Example 3-5 | Ultrafine Particle Titanium Oxide | 40 | 10 | 5 | | | |
| Comparative Example 3-6 | Plate-Shaped Barium Sulfate | 40 | 10 | 5 | | | |
| Comparative Example 3-7 | Aluminum Oxide | 40 | 10 | 5 | | | |
| Comparative Example 3-8 | Silica | 40 | 10 | 5 | | | |
| Comparative Example 3-9 | Talc | 40 | 10 | | 5 | | |
| Comparative Example 3-10 | Talc | 40 | 10 | | 3 | | |
| Comparative Example 3-11 | Ultrafine Particle Titanium Oxide | 40 | 10 | | 5 | | |
| Comparative Example 3-12 | Pigment-Grade Titanium Oxide | 40 | 10 | | 5 | | |
| Comparative Example 3-13 | Iron Oxide (Red Pigment) | 40 | 10 | | 5 | | |
| Comparative Example 3-14 | Plate-Shaped Barium Sulfate | 40 | 10 | | 5 | | |
| Comparative Example 3-15 | Aluminum Oxide | 40 | 10 | | 5 | | |
| Comparative Example 3-16 | Talc | 40 | 10 | | | 5 | |
| Comparative Example 3-17 | Talc | 40 | 10 | | | 3 | |
| Comparative Example 3-18 | Pigment-Grade Titanium Oxide | 40 | 10 | | | 5 | |
| Comparative Example 3-19 | Ultrafine Particle Titanium Oxide | 40 | 10 | | | 5 | |
| Comparative Example 3-20 | Talc | 40 | 10 | | | | 5 |
| Comparative Example 3-39 | Sericite | 40 | 10 | 5 | | | |

TABLE 5-2

Details on method of treating various powders with Nε-lauroyl lysine crystals

| | Powder Type | Treatment of Powder by Wet Treatment Method Mass percent of $N^\varepsilon$-lauroyl lysine relative to 100 mass percent of powder (%) | Untreated Powder | Treatment of Powder by Mixing with Composite Treatment Machine Mass percent of commercially available $N^\varepsilon$-lauroyl lysine crystals (D90 = 15.7 μm) relative to 100 mass percent of powder (%) |
|---|---|---|---|---|
| Comparative Example 3-21 | Talc | 5 | | |

TABLE 5-2-continued

Details on method of treating various powders with Nε-lauroyl lysine crystals

| | Powder Type | Treatment of Powder by Wet Treatment Method Mass percent of N$^\varepsilon$-lauroyl lysine relative to 100 mass percent of powder (%) | Untreated Powder | Treatment of Powder by Mixing with Composite Treatment Machine Mass percent of commercially available N$^\varepsilon$-lauroyl lysine crystals (D90 = 15.7 μm) relative to 100 mass percent of powder (%) |
|---|---|---|---|---|
| Comparative Example 3-22 | Sericite | 5 | | |
| Comparative Example 3-23 | Talc | | Untreated Powder | |
| Comparative Example 3-24 | Sericite | | Untreated Powder | |
| Comparative Example 3-25 | Iron Oxide (Yellow Pigment) | | Untreated Powder | |
| Comparative Example 3-26 | Iron Oxide (Black Pigment) | | Untreated Powder | |
| Comparative Example 3-27 | Iron Oxide (Red Pigment) | | Untreated Powder | |
| Comparative Example 3-28 | Ultrafine Particle Titanium Oxide | | Untreated Powder | |
| Comparative Example 3-29 | Pigment-Grade Titanium Oxide | | Untreated Powder | |
| Comparative Example 3-30 | Plate-Shaped Barium Sulfate | | Untreated Powder | |
| Comparative Example 3-31 | Aluminum Oxide | | Untreated Powder | |
| Comparative Example 3-32 | Cellulose | | Untreated Powder | |
| Comparative Example 3-33 | Cellulose Particle | | Untreated Powder | |
| Comparative Example 3-34 | Starch | | Untreated Powder | |
| Comparative Example 3-35 | Silica | | Untreated Powder | |
| Comparative Example 3-36 | Hexagonal Plate-Shaped Zinc Oxide | | Untreated Powder | |
| Comparative Example 3-37 | Talc | | | 5 |
| Comparative Example 3-38 | Pigment-Grade Titanium Oxide | 5 | | |

TABLE 5-3

Details on method of treating various powders with Nε-lauroyl lysine crystals

| | | Treatment of Powder by Simple Mixing Method | | |
|---|---|---|---|---|
| | Powder Type | Rotating Speed of Mixer Blades m/s | Mixing Time (Min) | Mass percent of N$^\varepsilon$-lauroyl lysine crystals of Example 2-1 relative to 100 mass percent of powder (%) |
| Example 3-1 | Talc | 40 | 10 | 5 |
| Example 3-2 | Talc | 40 | 10 | 3 |
| Example 3-3 | Sericite | 40 | 10 | 5 |
| Example 3-4 | Talc | 40 | 10 | 7 |
| Example 3-5 | Talc | 40 | 10 | 10 |
| Example 3-6 | Talc | 40 | 20 | 5 |
| Example 3-7 | Talc | 40 | 30 | 5 |
| Example 3-8 | Talc | 40 | 60 | 5 |
| Example 3-9 | Iron Oxide (Yellow Pigment) | 40 | 10 | 5 |
| Example 3-10 | Iron Oxide (Black Pigment) | 40 | 10 | 5 |
| Example 3-11 | Iron Oxide (Red Pigment) | 40 | 10 | 5 |
| Example 3-12 | Ultrafine Particle Titanium Oxide | 40 | 10 | 5 |

TABLE 5-3-continued

Details on method of treating various powders with Nε-lauroyl lysine crystals

Treatment of Powder by Simple Mixing Method

| | Powder Type | Rotating Speed of Mixer Blades m/s | Mixing Time (Min) | Mass percent of $N^\varepsilon$-lauroyl lysine crystals of Example 2-1 relative to 100 mass percent of powder (%) |
|---|---|---|---|---|
| Example 3-13 | Pigment-Grade Titanium Oxide | 40 | 10 | 5 |
| Example 3-14 | Hexagonal Plate-Shaped Zinc Oxide | 40 | 10 | 5 |
| Example 3-15 | Plate-Shaped Barium Sulfate | 40 | 10 | 5 |
| Example 3-16 | Aluminum Oxide | 40 | 10 | 5 |
| Example 3-17 | Cellulose | 40 | 10 | 5 |
| Example 3-18 | Cellulose Particle | 40 | 10 | 5 |
| Example 3-19 | Starch | 40 | 10 | 5 |
| Example 3-20 | Starch | 40 | 10 | 20 |
| Example 3-21 | Silica | 40 | 10 | 5 |

TABLE 5-4

Details on method of treating various powders with mixture crystals of $N^\varepsilon$-octanoyl lysine and $N^\varepsilon$-lauroyl lysine Treatment of Powder by Simple Mixing Method

| | Powder Type | Rotating Speed of Mixer Blades m/s | Mixing Time (Min) | Mass percent of crystals of Example 2-3 relative to 100 mass percent of powder (%) | Mass percent of crystals of Example 2-4 relative to 100 mass percent of powder (%) | Mass percent of crystals of Example 2-5 relative to 100 mass percent of powder (%) | Mass percent of crystals of Example 2-6 relative to 100 mass percent of powder (%) |
|---|---|---|---|---|---|---|---|
| Example 3-22 | Talc | 40 | 10 | 5 | | | |
| Example 3-23 | Talc | 40 | 10 | | 5 | | |
| Example 3-24 | Talc | 40 | 10 | | | 5 | |
| Example 3-25 | Talc | 40 | 10 | | | | 5 |

Method of Treating Powder by Simple Mixing:

Various powders and $N^\varepsilon$-lauroyl lysine crystals or the mixture crystals of $N^\varepsilon$-octanoyl lysine and $N^\varepsilon$-lauroyl lysine were added to a Henschel mixer (FM 10C/I manufactured by NIPPON COKE & ENGINEERING. CO., LTD.) and agitated and mixed at room temperature. In addition, the temperature in the mixer was controlled so that the maximum temperature in the mixer was lower than 80° C. when the temperature was gradually increased by the mixing operation.

Method of Treating Powder by Wet Treatment Method:

In 1.5% alkaline aqueous solution, 5 g of $N^\varepsilon$-lauroyl lysine was dissolved, and 100 g of each powder was added to the obtained solution, suspended (powder content of 20% by weight), and agitated for 30 minutes. Next, hydrochloric acid was added for neutralization to pH 7.0, and agitation was continued for another 30 minutes. After that, it was repeatedly filtered and washed with water, and then dried at 80° C. for 30 hours. The dried material was crushed to obtain various powders with a film of $N^o$-lauroyl lysine.

Method of Treating Powder by Mixing in Composite Treatment Machine:

The hybridization system NHS-1-2L (manufactured by Nara Machinery Co., Ltd.) was used to add 5 g of $N^\varepsilon$-lauroyl lysine crystals with a median diameter of 20 μm to 200 g of powder, and the mixing treatment was carried out at a rotor speed of 100 m/s for 3 minutes.

Figure 25:
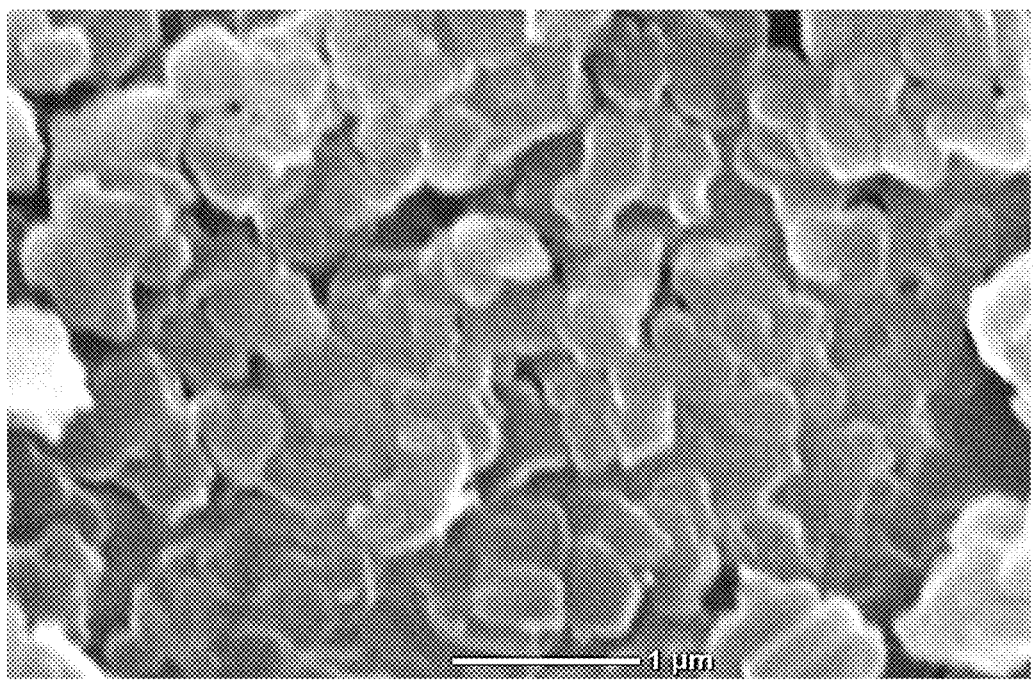
FIG. 25 is an SEM image of the crystals of Example 2-1.

Microscopic Observation of Treated State:

The crystals obtained in Example 2-1 were deposited with gold-platinum and then observed with a scanning electron microscope (JEOL JCM-6000 PLUS), and images of the surface conditions were recorded. FIG. 25 presents the recorded images.

Calculation of Particle Diameter of $N^\varepsilon$-Lauroyl Lysine Crystals Coating Surface of Treated Powder:

The treated powder of Examples 3-19 was deposited with gold-platinum and then observed with a scanning electron microscope (JEOL JCM-6000 PLUS). The obtained images were used to measure the particle diameter of 500 plate-shaped $N^6$-lauroyl lysine crystals attached to the powder surface. Among the $N^\varepsilon$-lauroyl lysine crystals, the number of $N^\varepsilon$-lauroyl lysine crystals with a particle diameter of 1.8 μm or less was 483 (96.6%).

Calculation of Particle Diameter of Mixture Crystal of $N^\varepsilon$-Octanoyl Lysine and $N^\varepsilon$-Lauroyl Lysine Coating Surface of Treated Powder:

The treated powder of Examples 3-24 was deposited with gold-platinum and then observed with a scanning electron microscope (JEOL JCM-6000 PLUS). The obtained images were used to measure the particle diameter of 500 plate-shaped crystals attached to the powder surface. Among all the crystals, the number of plate-shaped crystals with a particle diameter of 1.8 μm or less was 461 (92.2%), and the number of plate-shaped crystals with 2.8 μm or less was 489 (97.8%).

Calculation of Coverage Rate of Surface of Treated Powder by $N^\varepsilon$-Lauroyl Lysine Crystals:

The treated powder of Examples 3-19 was deposited with gold-platinum and then observed with a scanning electron microscope (JEOL JCM-6000 PLUS). The area of 1 cm² of the obtained images of the powder that was not covered with plate-shaped $N^\varepsilon$-lauroyl lysine crystals was identified and the area was calculated by ImageJ. The same treatment was applied to 20 powders, and it was found that on average 0.67 cm² (67%) of the image of the powder was coated with $N^\varepsilon$-lauroyl lysine.

Example 4

Various powders were mixed in the ratios presented in Table 6 by the method of treating powders by simple mixing. The obtained mixed powder had good water repellency and oil repellency, a soft feel, and excellent adhesion to the skin.

TABLE 6

| Raw Material Name | Model Number | Manufacturer | Amount Blended (Mass Percent %) |
|---|---|---|---|
| Talc | JA-46R | Asada Milling Co., Ltd. | 55 |
| Sericite | Sericite FSE | Sanshin Mining Ind. Co., Ltd. | 20 |
| Mica | Y-2300X | Yamaguchi Mica Co., Ltd. | 8 |
| Pigment-Grade Titanium Oxide | CR-50 | Ishihara Sangyo Kaisha, Ltd. | 10 |
| Iron Oxide: Yellow (Dimethicone-Treated) | SA-YELLOW LL-100P | Miyoshi Kasei, Inc. | 1.3 |
| Iron Oxide: Red (Dimethicone-Treated) | SA-RED R-516PS | Miyoshi Kasei, Inc. | 0.5 |
| Iron Oxide: Black (Dimethicone-Treated) | SA-BLACK BL-100P | Miyoshi Kasei, Inc. | 0.2 |
| $N^\varepsilon$-Lauroyl Lysine Crystals of Example 2-1 | | | 5 |
| Total | | | 100 |
| Rotating Speed of Mixer Blades m/s | | | 40 |
| Mixing Time (Min) | | | 30 |

Example 5-1

Various powders were mixed in the ratios presented in Table 7 by the method of treating powders by simple mixing. The obtained mixed powder had good water repellency and oil repellency, a soft feel, and excellent adhesion to the skin.

TABLE 7

| Raw Material Name | Model Number | Manufacturer | Amount Blended (Mass Percent %) |
|---|---|---|---|
| Powder of Example 3-1 | — | — | 60 |
| Powder of Example 3-3 | — | — | 20 |
| Powder of Example 3-13 | — | — | 10 |
| Mica | Y-2300X | Yamaguchi Mica Co., Ltd. | 8 |
| Iron Oxide: Yellow (Dimethicone-Treated) | SA-YELLOW LL-100P | Miyoshi Kasei, Inc. | 1.3 |
| Iron Oxide: Red (Dimethicone-Treated) | SA-RED R-516PS | Miyoshi Kasei, Inc. | 0.5 |
| Iron Oxide: Black (Dimethicone-Treated) | SA-BLACK BL-100P | Miyoshi Kasei, Inc. | 0.2 |
| Total | | | 100 |
| Rotating Speed of Mixer Blades m/s | | | 40 |
| Mixing Time (Min) | | | 30 |

Comparative Example 5-1

Various powders were mixed in the ratios presented in Table 8 by the method of treating powders by simple mixing. The obtained mixed powder didn't have sufficient water repellency and oil repellency, nor did it have a sufficient soft feel or adhesion to the skin.

TABLE 8

| Raw Material Name | Model Number | Manufacturer | Amount Blended (Mass Percent %) |
|---|---|---|---|
| Powder of Comparative Example 3-21 | — | — | 60 |
| Powder of Comparative Example 3-22 | — | — | 20 |
| Powder of Comparative Example 3-38 | — | — | 10 |
| Mica | Y-2300X | Yamaguchi Mica Co., Ltd. | 8 |
| Iron Oxide: Yellow (Dimethicone-Treated) | SA-YELLOW LL-100P | Miyoshi Kasei, Inc. | 1.3 |
| Iron Oxide: Red (Dimethicone-Treated) | SA-RED R-516PS | Miyoshi Kasei, Inc. | 0.5 |
| Iron Oxide: Black (Dimethicone-Treated) | SA-BLACK BL-100P | Miyoshi Kasei, Inc. | 0.2 |
| Total | | | 100 |
| Rotating Speed of Mixer Blades m/s | | | 40 |
| Mixing Time (Min) | | | 30 |

Comparative Example 5-2

Various powders were mixed in the ratios presented in Table 9 by the method of treating powders by simple mixing. The obtained mixed powder had almost no water repellency and oil repellency, nor did it have a sufficient soft feel or adhesion to the skin.

TABLE 9

| Raw Material Name | Model Number | Manufacturer | Amount Blended (Mass Percent %) |
|---|---|---|---|
| Powder of Comparative Example 3-23 | — | — | 60 |
| Powder of Comparative Example 3-24 | — | — | 20 |
| Powder of Comparative Example 3-29 | — | — | 10 |
| Mica | Y-2300X | Yamaguchi Mica Co., Ltd. | 8 |
| Iron Oxide: Yellow (Dimethicone-Treated) | SA-YELLOW LL-100P | Miyoshi Kasei, Inc. | 1.3 |
| Iron Oxide: Red (Dimethicone-Treated) | SA-RED R-516PS | Miyoshi Kasei, Inc. | 0.5 |
| Iron Oxide: Black (Dimethicone-Treated) | SA-BLACK BL-100P | Miyoshi Kasei, Inc. | 0.2 |
| Total | | | 100 |
| Rotating Speed of Mixer Blades m/s | | | 40 |
| Mixing Time (Min) | | | 30 |

Example 6

Various powders were mixed in the ratios presented in Table 10 for 10 minutes using an impact-type grinder (atomizer manufactured by Dalton Co., Ltd.). The obtained mixed powder had good water repellency and oil repellency and a soft feel. Furthermore, it had excellent uniform color development properties of pigments.

TABLE 10

| Raw Material Name | Model Number | Manufacturer | Amount Blended (Mass Percent %) |
|---|---|---|---|
| Powder of Example 3-1 | — | — | 60 |
| Powder of Example 3-3 | — | — | 20 |
| Powder of Example 3-13 | — | — | 10 |
| Mica | Y-2300X | Yamaguchi Mica Co., Ltd. | 8 |
| Iron Oxide: Yellow (Dimethicone-Treated) | SA-YELLOW LL-100P | Miyoshi Kasei, Inc. | 1.3 |
| Iron Oxide: Red (Dimethicone-Treated) | SA-RED R-516PS | Miyoshi Kasei, Inc. | 0.5 |
| Iron Oxide: Black (Dimethicone-Treated) | SA-BLACK BL-100P | Miyoshi Kasei, Inc. | 0.2 |
| Total | | | 100 |

Example 7

Various powders were mixed in the ratios presented in Table 11 by the method of treating powders by simple mixing. The water repellency and oil repellency of the obtained mixed powder were calculated as follows.

Water repellency=100+(amount of powder floating on solvent after 60 minutes/amount of powder floating on solvent at 0 minutes)

Oil repellency=100×(amount of powder floating on solvent after 5 minutes/amount of powder floating on solvent at 0 minutes)

Based on the values obtained from the above formulas, the evaluation was conducted according to the following evaluation criteria to compare the water repellency and oil repellency of the mixed powder. Table 11 presents the results.

Evaluation of Degree of Water Repellency
1) Water repellency value of 60% or more: very favorable (A)
2) Water repellency value higher than 30% and lower than 60%: somewhat favorable (B)
3) Water repellency value higher than 10% and lower than 30%: not very favorable (C)
4) Water repellency value less than 10%: not favorable at all (D)

Evaluation of Degree of Oil Repellency
1) Oil repellency value of 50% or more: very favorable (A)
2) Oil repellency value higher than 20% and lower than 50%: somewhat favorable (B)
3) Oil repellency value higher than 5% and lower than 20%: not very favorable (C)
4) Oil repellency value less than 5%: not favorable at all (D)

In addition, four expert panelists evaluated the softness feel and shine of the various mixtures when applied according to the following criteria.

Evaluation of Softness when Applied
1) Very soft and good feel when applied . . . 4 points
2) Slightly soft and good feel when applied . . . 3 points
3) Slightly hard and not very good feel when applied . . . 2 points
4) Hard and not good at all when applied . . . 1 point Shine when Applied
1) Very good natural shine after application . . . 4 points
2) Slight shine after application . . . 3 points
3) Not much shine after application . . . 2 points
4) No shine at all after application . . . 1 point The following judgments were made based on the average scores of the evaluation of the four expert panelists. Table 11 presents the results.

Average evaluation score of 3.5 or higher: very favorable (A)

Average evaluation score of 2.5 or higher and less than 3.5: somewhat favorable (B)

Average evaluation score of 1.5 or higher and less than 2.5: not very favorable (C)

Average evaluation score of less than 1.5: not favorable at all (D)

TABLE 11

Effect of mixing with silicon-containing powder

| Raw Material Name | Shape and Property | Model Number | Manufacturer | Powder Crystallinity | 7-1 | 7-2 | 7-3 | 7-4 | 7-5 | 7-6 | 7-7 | 7-8 |
|---|---|---|---|---|---|---|---|---|---|---|---|---|
| Nε-Lauroyl Lysine Crystals of Example 2-1 | | | | — | 5 | 8 | 10 | 8 | 8 | 8 | 8 | 8 |
| Commercially Available Nε-Lauroyl Lysine Crystals (D90 = 15.7 μm) | | "Amihope" LL | Ajinomoto Co., Inc. | — | | | | | | | | |
| Nε-Lauroyl Lysine Crystals of Comparative Example 1-3 | | | | — | | | | | | | | |
| Anhydrous Silicic Acid | Leaf-Shaped Silica | Oliver DR | Osaka Gas Chemicals Co., Ltd. | Amorphous | | | | | 92 | | | |
| Anhydrous Silicic Acid | Non-Porous Silica | Sunsphere NP-30 | AGC Si-Tech Co., Ltd. | Amorphous | | | | | | | 92 | |

TABLE 11-continued

Effect of mixing with silicon-containing powder

| Raw Material Name | Shape and Property | Model Number | Manufacturer | Powder Crystallinity | | | | | | | |
|---|---|---|---|---|---|---|---|---|---|---|---|
| Anhydrous Silicic Acid Porous Silica | Sunsphere H-51 | AGC Si-Tech Co., Ltd. | Amorphous | | | | | | | 92 | |
| Anhydrous Silicic Acid Porous Silica | Sunsphere L-51 | AGC Si-Tech Co., Ltd. | Amorphous | | | | | | | | 92 |
| Anhydrous Silicic Acid Semi-porous Silica | Silica Micro Bead P-1500 | JGC C&C Ltd. | Amorphous | 95 | 92 | 90 | | | | | |
| Bentonite | Oliver BR | Osaka Gas Chemicals Co., Ltd. | Crystalline | | | | | | | | 92 |
| Hydrated Silica | Oliver GR | Osaka Gas Chemicals Co., Ltd. | Amorphous | | | | | | | | |
| Cubic Shape Na Aluminosilicate | Oliver AR | Osaka Gas Chemicals Co., Ltd. | Crystalline | | | | | | | | |
| (Al/Ca/Na) Silicate | Oliver CR | Osaka Gas Chemicals Co., Ltd. | Crystalline | | | | | | | | |
| (Na/Mg) Silicate | Oliver ER | Osaka Gas Chemicals Co., Ltd. | Crystalline | | | | | | | | |
| | | Total (Mass Percent %) | | 100 | 100 | 100 | 100 | 100 | 100 | 100 | 100 |
| | | Water Repellency | | A | A | A | A | A | A | A | A |
| | | Oil Repellency | | B | A | A | A | A | A | A | A |
| | | Texture Softness | | A | A | A | A | A | A | A | A |
| | | Shine when Applied | | A | A | A | A | A | A | A | A |

| Raw Material Name | Shape and Property | Model Number | Manufacturer | Powder Crystallinity | Example 7-9 | Example 7-10 | Example 7-11 | Example 7-12 | Comparative Example 7-1 | Comparative Example 7-2 |
|---|---|---|---|---|---|---|---|---|---|---|
| Nε-Lauroyl Lysine Crystals of Example 2-1 | | | | — | 8 | 8 | 8 | 8 | | |
| Commercially Available Nε-Lauroyl Lysine Crystals (D90 = 15.7 μm) | "Amihope" LL | | Ajinomoto Co., Inc. | — | | | | | | |
| Nε-Lauroyl Lysine Crystals of Comparative Example 1-3 | | | | — | | | | | | |
| Anhydrous Silicic Acid Leaf-Shaped Silica | Oliver DR | | Osaka Gas Chemicals Co., Ltd. | Amorphous | | | | | | |
| Anhydrous Silicic Acid Non-Porous Silica | Sunsphere NP-30 | | AGC Si-Tech Co., Ltd. | Amorphous | | | | | | |
| Anhydrous Silicic Acid Porous Silica | Sunsphere H-51 | | AGC Si-Tech Co., Ltd. | Amorphous | | | | | | |
| Anhydrous Silicic Acid Porous Silica | Sunsphere L-51 | | AGC Si-Tech Co., Ltd. | Amorphous | | | | | | |
| Anhydrous Silicic Acid Semi-porous Silica | Silica Micro Bead P-1500 | | JGC C&C Ltd. | Amorphous | | | | | | |
| Bentonite | Oliver BR | | Osaka Gas Chemicals Co., Ltd. | Crystalline | | | | | | |
| Hydrated Silica | Oliver GR | | Osaka Gas Chemicals Co., Ltd. | Amorphous | 92 | | | | | |
| Cubic Shape Na Aluminosilicate | Oliver AR | | Osaka Gas Chemicals Co., Ltd. | Crystalline | | | | | | |
| (Al/Ca/Na) Silicate | Oliver CR | | Osaka Gas Chemicals Co., Ltd. | Crystalline | | | 92 | | | |

TABLE 11-continued

| Effect of mixing with silicon-containing powder | | | | | | | | | |
|---|---|---|---|---|---|---|---|---|---|
| (Na/Mg) Silicate | Oliver ER | Osaka Gas Chemicals Co., Ltd. | Crystalline | | | | | 92 | |
| | | Total (Mass Percent %) | | 100 | 100 | 100 | 100 | 100 | 100 |
| | | Water Repellency | | A | A | A | A | B | B |
| | | Oil Repellency | | A | A | A | A | C | C |
| | | Texture Softness | | A | A | A | A | C | C |
| | | Shine when Applied | | A | A | A | A | B | D |

Example 8-1 and Comparative Example 8-1

Cleanser compositions were prepared using the components presented in Table as follows.

Component A was dispersed in component B at room temperature. In addition, component C was added and agitated at room temperature to make a uniform solution. Furthermore, component D was added and agitated until homogeneous using HOMO DISPER. Component E was added to adjust the pH to 5.4, and then component F was added and mixed uniformly to obtain the cleanser composition.

The obtained cleanser composition was stored for 1 month under cyclic temperature conditions of −5° C. to 40° C. (The temperature in the chamber was kept at −5° C. for 12 hours, increased from −5° C. to 40° C. over 3 hours, kept at 40° C. for 12 hours, then cooled from 40° C. to −5° C. for another 3 hours, and kept at −5° C. for 12 hours. The temperature was repeatedly changed in such a cycle). The degree of pearlization of the composition before and after storage was visually checked. The composition of Example 8-1 maintained the same pearl effects as immediately after preparation, while the composition of Comparative Example 8-1 could hardly maintain the pearl effects.

In addition, four expert panelists evaluated the conditioning effects of the cleanser compositions of Example 8-1 and Comparative Example 8-1 on the hair and skin after use, and as a result, all the panelists evaluated that the composition of Example 8-1 had higher conditioning effects on the hair and skin compared to the composition of Comparative Example 8-1.

TABLE 12

Cleanser Composition

| | Raw Material Name | Model Number | Manufacturer | Example 8-1 | Comparative Example 8-1 |
|---|---|---|---|---|---|
| A | Xanthan Gum | Rhodicare T | Rhodia Nicca, Ltd. | 1.00 | 1.00 |
| B | Water | | | 49.00 | 49.00 |
| C | Sodium Cocoyl Glutamate (25%) | "Amisoft" CS-22 | Ajinomoto Co., Inc. | 10.00 | 10.00 |
| | Coco-Glucoside (52%) | Plantacare 818 up | Cognis Japan Ltd. | 6.00 | 6.00 |
| | Glyceryl Caprylate | Sunsoft No. 700-P2 | Taiyo Kagaku Co., Ltd. | 2.00 | 2.00 |
| | Arginine | | Ajinomoto Co., Inc. | 0.30 | 0.30 |
| | Water | | | 27.15 | 27.15 |
| | Decyl Glucoside (50%) | Plantacare 2000 up | Cognis Japan Ltd. | 0.75 | 0.75 |
| | Lauryl Glucoside (50%) | Plantacare 1200 up | Cognis Japan Ltd. | 0.75 | 0.75 |
| D | Commercially Available $N^\varepsilon$-Lauroyl Lysine Crystals (D90 = 15.7 μm) | "Amihope" LL | Ajinomoto Co., Inc. | | 1.00 |
| | $N^\varepsilon$-Lauroyl Lysine Crystals of Example 2-2 | | | 1.00 | |
| E | 30% Citric Acid Aqueous Solution | | | 2.00 | 2.00 |
| F | Propyl Paraben | | | 0.05 | 0.05 |
| | | | Total (Mass Percent %) | 100.00 | 100.00 |
| | | | pH | 5.4 | 5.40 |
| | | | Viscosity (Type-B Viscometer, Rotor No. 3, 30 rpm, 30 sec., 25° C.) | 2000 mPa · s | 2000 mPa · s |

Example 9-1 and Comparative Example 9-1

Cleanser compositions were prepared using the components presented in Table as follows.

Component A was dispersed in component B at room temperature. Also, component E was agitated and dissolved at room temperature. In addition, component C and component D were each agitated and dissolved at 60° C. To component B, in which component A was dispersed, component C and component D were added, and agitated and mixed at 60° C. Furthermore, component E was added, and agitated and mixed, and then cooled to 50° C., and component F was added. The temperature was cooled to room temperature to obtain the cleanser composition.

Four expert panelists evaluated the effectiveness of the cleanser compositions of Example 9-1 and Comparative Example 9-1 in reducing the slimy feel of surfactants during use, and as a result, all the panelists evaluated that the composition of Example 9-1 was more effective in reducing the slimy feel of surfactants during use compared to the composition of Comparative Example 9-1.

TABLE 13

Cleanser Composition

| | Raw Material Name | Model Number | Manufacturer | Example 9-1 | Comparative Example 9-1 |
|---|---|---|---|---|---|
| A | Acrylate/Alkyl Acrylate (C10-30) Crosspolymer | Ultrez 20 | Nikko Chemicals Co., Ltd. | 1.00 | 1.00 |
| B | Water | | | 32.00 | 32.00 |
| C | BG | | | 6.00 | 6.00 |
| | Phenoxyethanol | | | 0.20 | 0.20 |
| D | Sodium Cocoyl Alanine (30%) | "Amilite" ACS-12 | Ajinomoto Co., Inc. | 6.00 | 6.00 |
| | Cocamidopropyl Betaine (30%) | Amphitol 55AB | Kao Corporation | 4.00 | 4.00 |
| | Na Laureth Sulfate (25%) | Emal 20C | Kao Corporation | 14.00 | 14.00 |
| | Polyquaternium-39 | Merquat PLUS 3330 | Matsumoto Trading Co., Ltd. | 1.00 | 1.00 |
| | N$^\varepsilon$-Lauroyl Lysine Crystals of Example 2-1 | | | 2.00 | |
| | Commercially Available N$^\varepsilon$-Lauroyl Lysine Crystals (D90 = 15.7 μm) | "Amihope" LL | Ajinomoto Co., Inc. | | 2.00 |
| | Water | | | 7.79 | 7.79 |
| E | Na Hydroxide | | | 0.26 | 0.26 |
| | Water | | | 25.74 | 25.74 |
| F | Linalool (Fragrance) | | | 0.01 | 0.01 |
| | | | Total (Mass Percent %) | 100.00 | 100.00 |
| | | | pH | 5.8 | 5.8 |
| | | | Viscosity (Type-B Viscometer, Rotor No. 3, 12 rpm, 30 sec., 25° C.) | 7800 mPa · s | 7800 mPa · s |

Evaluation of Soft-Focus Effect of Powder:

To a black paper sheet, 50 mg of the powder was applied uniformly, and the light scattering ability of each powder was measured using the device GONIOPHOTOMETER GP-700 (Murakami Color Research Laboratory). The powder surface was irradiated with light at −45° to determine the ratio of the intensities of light scattered at 45° and 0° (intensity at 45°/intensity at 0°). The closer the value of this ratio is to 1, the higher the soft-focus effect of the powder can be evaluated. In addition, the rate of improvement in the soft-focus effect of the powder by treatment with N$^\varepsilon$-lauroyl lysine crystals was also compared.

TABLE 14

Evaluation of improved soft-focus effect of powder

| Sample Name | Light Intensity at 45° | Light Intensity at 0° | Soft-Focus Effect (Intensity at 45°/ Intensity at 0°) | Soft Focus Effect Improvement Rate (%) |
|---|---|---|---|---|
| Powder of Comparative Example 3-24 | 96.35 | 48.43 | 1.99 | — |
| Powder of Example 3-3 | 80.64 | 71.05 | 1.13 | 42.95 |
| Powder of Comparative Example 3-30 | 90.57 | 37.59 | 2.41 | — |
| Powder of Example 3-15 | 63.37 | 42.73 | 1.48 | 62.47 |

The results in Table 14 indicate that treatment with $N^\varepsilon$-lauroyl lysine crystals improves the soft-focus effect of the plate-shaped powder.

Example 10-1 and Comparative Example 10-1

Lip cosmetics were prepared using the components presented in Table IS as follows.

Component A was heated and dissolved at 105±5° C., and component B was added to component A, and heated and dissolved at 90° C. Component C was further added, and heated and mixed at 90° C., and then dispersed with three rolls, and after that component D was added. Component E was added, and heated and mixed at 90° C., followed by defoaming. The mixture was filled into a sink mold at a filling temperature of 90° C., and after cooling, the mixture was loaded into a container.

The lip cosmetic of Example 10-1 showed better color development, less color unevenness, and better color uniformity compared to Comparative Example 10-1. Furthermore, there was no perspiration, and the product was stable.

TABLE 15

Lip cosmetics

| | Raw Material Name | Example 10-1 | Comparative Example 10-1 |
|---|---|---|---|
| A | Polyethylene Wax | 2.8 | 2.8 |
| | Triethylhexanoin | 15 | 15 |
| B | Candelilla Wax | 1 | 1 |
| | Paraffin Wax | 7 | 7 |
| | Microcrystalline Wax | 6 | 6 |
| | Hydrogenated Polyisobutene | 12 | 12 |
| | Dipentaerythrityl Hexa (Hydroxystearate/Stearate/Rosinate) | 5 | 5 |
| | Isotridecyl Isononanoate | 10 | 10 |
| | Trimethylolpropane Triisostearate | 5 | 5 |
| | Bis (Behenyl/Isostearyl/Phytosteryl) Dimer Dilinoleyl Dimer Dilinoleate | 3 | 3 |
| | (Phytosteryl/Octyldodecyl) Lauroyl Glutamate | 2 | 2 |
| | Tocopherol | 0.1 | 0.1 |
| | Preservative (Chlorphenesin) | 0.3 | 0.3 |
| C | Titanium Oxide, Mica, Silica (Composite Powder) | 0.5 | 0.5 |
| | Mica, Titanium Oxide (Composite Powder) | 2 | 2 |
| D | Red 201 | 0.3 | 0.3 |
| | Red 202 | 0.6 | 0.6 |
| | Powder of Example 3-11 | 0.7 | — |
| | Powder of Comparative Example 3-26 | — | 0.7 |
| | Powder of Comparative Example 3-4 | — | 2 |
| | Powder of Example 3-13 | 2 | — |
| | Polyglyceryl-2 Triisostearate | 3 | 3 |
| E | Polyglyceryl-2 Triisostearate | 21.7 | 21.7 |
| | Total (Mass Percent %) | 100 | 100 |

Example 11-1 and Comparative Example 11-1

Leave-on cosmetics were prepared using the components presented in Table 16 as follows.

Component A and component B were each heated to 80° C. and dissolved, and then component A was added to component B with agitation. The mixture was emulsified with a homomixer (3000 rpm, 3 minutes, 80° C.) and cooled to room temperature to obtain a leave-on cosmetic.

The leave-on cosmetic of Example 11-1 had better stability and antiseptic properties compared to Comparative Example 11-1. Furthermore, it had an excellent moist feel after application, and its shine was further improved by application.

TABLE 16

Leave-on cosmetics

| | Raw Material Name | Example 11-1 | Comparative Example 11-1 |
|---|---|---|---|
| A | UV Absorber (Ethylhexyl Methoxycinnamate) | 2.00 | 2.00 |
| | Squalane | 6.00 | 6.00 |
| | Cetyl Ethylhexanoate | 3.00 | 3.00 |
| | Cetanol | 2.80 | 2.80 |
| | Stearic Acid | 2.40 | 2.40 |
| | Propylene Glycol Stearate | 1.20 | 1.20 |
| | Glyceryl Stearate (SE) | 3.30 | 3.30 |
| | Polysorbate 60 | 0.50 | 0.50 |
| | PEG-40 Stearate | 1.50 | 1.50 |
| | Tocopherol | 0.05 | 0.05 |
| | Crystals Obtained in Example 2-1 | 5.00 | — |
| | Crystals Obtained in Comparative Example 1-3 | — | 5.00 |
| | Phytosteryl Macadamiate | 1.00 | 1.00 |
| | Preservative (Pentylene Glycol) | 1.00 | 1.00 |
| B | BG | 5.00 | 5.00 |
| | Xanthan Gum | 0.10 | 0.10 |
| | Preservative (Sodium Dehydroacetate) | 0.10 | 0.10 |
| | Water | 65.05 | 65.05 |
| | Total (Mass Percent %) | 100.0 | 100.0 |

Example 12-1 and Comparative Example 12-1

Eye makeup cosmetics were prepared using the components presented in Table as follows.

Component A was mixed for 10 minutes, and then component B was added to component A and mixed for another 20 minutes. Component C was mixed for 10 minutes using a mixer (FM 10C/I manufactured by NIPPON COKE & ENGINEERING. CO., LTD.), then added to the mixture of component A+component B and mixed for another 5 minutes. The obtained mixture was filled into a container and compressed using a press machine to obtain the desired eye makeup cosmetic.

Four expert panelists evaluated the pearlescence, gloss, shine, and color development of the eye makeup cosmetics of Example 12-1 and Comparative Example 12-1 after application, and as a result, all the panelists evaluated that the eye makeup cosmetic of Example 12-1 had a higher pearlescence, gloss, shine, and color development after application compared to the eye makeup cosmetic of Comparative Example 12-1. The eye makeup cosmetic of Example 12-1 can be produced using a small amount of oil agent and has excellent use feel. In Example 12-1, the gloss of pearl powder and colored pearl pigment did not decrease, but rather, the gloss increased.

TABLE 17

Eye makeup cosmetics

| Major Classification of Raw Material | Raw Material Name | Example 12-1 | Comparative Example 12-1 |
|---|---|---|---|
| A Powder | Boron Nitride | 12.2 | 12.2 |
| | Talc | 12 | 12 |
| | Mg Myristate | 5 | 5 |
| | Silica | 5 | 5 |
| B Oil Agent | Glyceryl Tri(Caprylate/Caprate) | 8 | 8 |
| A Coloring Pigment | Iron Oxide (Red) | 1 | 1 |
| | Iron Oxide (Yellow) | 0.3 | 0.3 |
| | Powder of Example 3-10 | 1.5 | — |
| | Powder of Comparative Example 3-26 | — | 1.5 |
| C Pearl Powder | (Ca/Na) Borosilicate | 5 | 5 |
| Colored Pearl Pigment (Composite Powder) | Synthetic Gold Mica, Titanium Oxide, Iron Oxide, Tin Oxide | 10 | 10 |
| | Mica, Titanium Oxide, Iron Oxide | 10 | 10 |
| | Mica, Titanium Oxide, Iron Oxide, Silica, Tin Oxide | 8 | 8 |
| | Synthetic Gold Mica, Titanium Oxide, Carmine | 1 | 1 |
| | Mica, Titanium Oxide, Iron Oxide, Chromium Oxide | 8 | 8 |
| | (Ca/Al) Borosilicate, Titanium Oxide, Silica, Tin Oxide, Dimethicone Crosspolymer | 5 | 5 |
| | Mica, Titanium Oxide, Iron Oxide, Prussian Blue | 3 | 3 |
| $N^\varepsilon$-Lauroyl Lysine | Crystals Obtained in Example 2-1 | 5 | — |
| | Crystals Obtained in Comparative Example 2-2 | — | 5 |
| | Total (Mass Percent %) | 100 | 100 |

Example 13-1 and Comparative Example 13-1

Make-up cosmetics were prepared using the components presented in Table 18 as follows.

Component B was mixed for 10 minutes, and then component C was added to component B, and component B was dispersed in component C using the disperser DISPER. Component A was gradually added to component B+component C and emulsified uniformly using a homomixer. After the emulsification was completed, component D was added and further mixed, and the mixture was cooled to room temperature to obtain the desired make-up cosmetic.

The makeup cosmetic of Example 13-1 had excellent emulsion stability, improved shine after application, and improved unevenness of pigments compared to Comparative Example 13-1. Furthermore, it had improved makeup lasting and good antiseptic properties, and was excellent in moist feel after application.

TABLE 18

Makeup cosmetics

| | Raw Material Name | Example 12-1 | Comparative Example 12-1 |
|---|---|---|---|
| A | Water | 55.6 | 55.6 |
| | 1,3-Butylene Glycol | 5 | 5 |
| | Glycerin | 2 | 2 |
| | Caprylyl Glycol | 1 | 1 |
| | Preservative (Phenoxyethanol) | 0.5 | 0.5 |
| | Preservative (Glyceryl Caprylate) | 1 | 1 |
| | Na Ethylenediaminetetraacetate | 0.05 | 0.05 |
| B | Pigment-Grade Titanium Oxide (Treated with Na Stearyl Glutamate) | 6 | 6 |
| | Crystals Obtained in Example 2-1 | 2 | — |

TABLE 18-continued

Makeup cosmetics

| | Raw Material Name | Example 12-1 | Comparative Example 12-1 |
|---|---|---|---|
| | Crystals Obtained in Comparative Example 2-1 | — | 2 |
| | Synthetic Gold Mica, Titanium Oxide, Iron Oxide, Tin Oxide (Composite Powder) | 1 | 1 |
| | Iron Oxide (Red) | 0.2 | 0.2 |
| | Iron Oxide (Yellow) | 1.3 | 1.3 |
| | Iron Oxide (Black) | 0.1 | 0.1 |
| C | Pentaerythrityl Tetraisostearate | 5 | 5 |
| | Stearyl Alcohol | 3 | 3 |
| | Polysorbate 20 | 2 | 2 |
| | Sorbitan Sesquioleate | 2 | 2 |
| | Butylene Glycol Cocoate | 2 | 2 |
| | Ethyl Cellulose | 0.2 | 0.2 |
| | Tocopherol | 0.05 | 0.05 |
| D | Xanthan Gum (10% Aqueous Solution) | 10 | 10 |
| | Total (Mass Percent %) | 100 | 100 |

Example 14

A foundation was prepared using the components presented in Table 19 as follows.

Component B was uniformly mixed. Component A was mixed with a mixer for 1 minute, and then component B was added to component A and mixed for another seconds. To 8 g of the obtained mixture, 12 g of the dispersing solvent, water and ethanol (mixing ratio was water:ethanol=80:20), was added and dispersed while mixing. The obtained dispersion in an amount of 13 g was measured into a container, and while pressing it, tissue paper was used from above to fully absorb the dispersion solvent, water and ethanol. The composition compressed in the container was dried at 80° C. overnight to obtain the desired foundation.

The foundation of Example 14 had excellent adhesion after application and an excellent natural finish. Furthermore, the product itself had good formability and beautiful color. Furthermore, the causes of makeup smudge such as unevenness, oiliness, patchiness, dullness, and disappearance due to changes over time in the makeup film were reduced.

TABLE 19

Foundation

| | Raw Material Name | Example 14 |
|---|---|---|
| A | Talc | 62.36 |
| | Nylon-12 | 5 |
| | Crystals of Example 2-5 | 5 |
| | Mg Myristate | 5 |
| | (Diphenyl Dimethicone/Vinyl Diphenyl Dimethicone/Silsesquioxane) Crosspolymer | 5 |
| | Boron Nitride | 5 |
| | Synthetic Gold Mica | 5 |
| | Pigment-Grade Titanium Oxide | 1 |
| | Iron Oxide (Red) | 0.5 |
| | Iron Oxide (Yellow) | 1.2 |
| | Iron Oxide (Black) | 0.3 |
| B | Octyldodecyl Stearoyl Stearate | 1.6 |
| | Ethylhexyl Palmitate | 0.8 |
| | Hydrogenated Polyisobutene | 0.8 |
| | Dimethicone | 0.8 |
| | Pentaerythritol Tetra(2-Ethylhexanoate) | 0.4 |
| | Polysorbate 60 | 0.24 |
| | Total (Mass Percent %) | 100 |

Example 15

The composition for pencils was prepared using the components presented in Table 20 as follows.

Component A, a composition in Table 20, was mixed in a mixer (FM 10C/I manufactured by NIPPON COKE & ENGINEERING. CO., LTD.) for 5 minutes, and then component B was added to component A and mixed for another 10 minutes. Component C was dissolved at 100° C., added to component A+component B, and mixed for 10 minutes. Component D was added to the obtained mixture, mixed with three rolls, then filled into a container while heating, and baked to solidify.

The pencil obtained in Example 15 was resistant to lead breakage and had a high shine. Furthermore, it had excellent color development properties.

TABLE 20

Composition for pencils

| | Raw Material Name | Example 15 |
|---|---|---|
| A | Crystals Obtained in Example 2-1 | 5.4 |
| | Carbon Black (Coloring Agent) | 0.1 |
| | Soot | 3 |
| | Phthalocyanine Blue (Coloring Agent) | 0.5 |
| | Metal Stearate (Extender) | 3 |
| | Talc (Extender) | 9.6 |
| B | Powder of Example 3-1 | 45 |
| | Powder of Example 3-11 | 0.4 |

TABLE 20-continued

Composition for pencils

| | Raw Material Name | Example 15 |
|---|---|---|
| C | Acrylic Styrene Copolymer (Binder) | 2 |
| | Acrylic Butadiene Styrene Copolymer (Binder) | 5 |
| | Nitrocellulose (Binder) | 3 |
| | Stearic Acid (Adhesive) | 1 |
| | Paraffin Wax | 2 |
| D | Ethylhexyl Palmitate (Solvent) | 20 |
| | Total (Mass Percent %) | 100 |

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. An $N^\varepsilon$-lauroyl lysine crystal or a mixture crystal of $N^\varepsilon$-octanoyl lysine and $N^\varepsilon$-lauroyl lysine, wherein a 90% particle diameter D90 of a number-based distribution is 2.8 µm or less.

2. The $N^\varepsilon$-lauroyl lysine crystal or the mixture crystal of $N^\varepsilon$-octanoyl lysine and $N^\varepsilon$-lauroyl lysine according to claim 1, wherein a median diameter or average particle diameter of a volume-based distribution is 2.8 µm or less.

3. An $N^\varepsilon$-lauroyl lysine crystal or a mixture crystal of $N^\varepsilon$-octanoyl lysine and $N^\varepsilon$-lauroyl lysine, wherein a bulk density is 0.34 g/mL or less.

4. A method of producing unground $N^\varepsilon$-long chain acyl lysine crystals comprising:
    preparing a solution in which at least one $N^\varepsilon$-long chain acyl lysine is dissolved in an acidic or basic solvent containing at least one selected from water-soluble organic solvents and/or water, and
    adding the solution dropwise to an acidic solution with a pH of 0.2 or higher and a pH lower than 2.0 at a temperature of 20° C. or lower, thereby crystallizing $N^\varepsilon$-long chain acyl lysine crystals.

5. The $N^\varepsilon$-lauroyl lysine crystal or the mixture crystal of $N^\varepsilon$-octanoyl lysine and $N^\varepsilon$-lauroyl lysine, which is obtained by the production method of claim 4 and wherein a 90% particle diameter D90 of a number-based distribution is 2.8 µm or less.

6. The $N^\varepsilon$-lauroyl lysine crystal or the mixture crystal of $N^\varepsilon$-octanoyl lysine and $N^\varepsilon$-lauroyl lysine according claim 1, wherein the crystal contains $N^\varepsilon$-octanoyl lysine at a ratio of 99 mass percent or less.

7. A composition comprising the $N^\varepsilon$-lauroyl lysine crystal or the mixture crystal of $N^\varepsilon$-octanoyl lysine and $N^\varepsilon$-lauroyl lysine according to claim 1 at 0.01 to 99.9 mass percent.

8. A cosmetic or a topical agent comprising the $N^\varepsilon$-lauroyl lysine crystal or the mixture crystal of $N^\varepsilon$-octanoyl lysine and $N^\varepsilon$-lauroyl lysine according to claim 1 at 0.01 to 99.9 mass percent.

9. A cleanser composition comprising the $N^\varepsilon$-lauroyl lysine crystal or the mixture crystal of $N^\varepsilon$-octanoyl lysine and $N^\varepsilon$-lauroyl lysine according to claim 1 at 0.01 to 99.9 mass percent.

10. A treated powder obtained by mixing a powder with the $N^\varepsilon$-lauroyl lysine crystal or the mixture crystal of $N^\varepsilon$-octanoyl lysine and $N^\varepsilon$-lauroyl lysine according to claim 1.

11. The treated powder according to claim 10, wherein the powder comprises crystalline or amorphous powders of resin powders, silicon-containing powders, metal oxides, carbon-containing powders, fluorine-containing powders, metallic salts, boron-containing powders, and composite powders.

12. The treated powder according to claim 10, wherein of the $N^\varepsilon$-lauroyl lysine crystal coating a surface of the treated powder, a ratio of the $N^\varepsilon$-lauroyl lysine crystal with a particle diameter of 1.8 μm or less is 90% or more.

13. The treated powder according to claim 10, wherein of the mixture crystal of $N^\varepsilon$-octanoyl lysine and $N^\varepsilon$-lauroyl lysine coating a surface of the treated powder, a ratio of the crystal with a particle diameter of 2.8 μm or less is 90% or more.

14. A method of preparing a treated powder, comprising mixing a powder with the $N^\varepsilon$-lauroyl lysine crystal or the mixture crystal of $N^\varepsilon$-octanoyl lysine and $N^\varepsilon$-lauroyl lysine according to claim 1 in an amount to coat 40% or more of a powder surface area with the $N^\varepsilon$-lauroyl lysine crystal or the mixture crystal of $N^\varepsilon$-octanoyl lysine and $N^\varepsilon$-lauroyl lysine.

15. The method of preparation according to claim 14, wherein the mixing includes mixing by dry mixing that requires no solvent.

16. The method of preparation according to claim 14, wherein the mixing includes mixing with a mixer for 60 minutes or less.

17. The treated powder according to claim 10 which has water repellency.

18. The treated powder according to claim 10 which has oil repellency.

19. The treated powder according to claim 10 which has a soft-focus effect.

20. A composition comprising the treated powder according to claim 10 at 0.01 to 99.99 mass percent.

21. The composition according to claim 20, which is a cosmetic, a topical agent, or a cleanser.

* * * * *